United States Patent
Usui

(10) Patent No.: US 6,436,128 B1
(45) Date of Patent: *Aug. 20, 2002

(54) INK LIKE OR CREAM-LIKE EXOTHERMIC COMPOSITION, EXOTHERMIC DEVICE MADE THEREOF AND MANUFACTURING METHOD OF EXOTHERMIC DEVICE

(75) Inventor: Akio Usui, Tochigi (JP)

(73) Assignee: Kabushiki Kaisha Genchi Kenkyusho (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/676,851

(22) Filed: Jul. 8, 1996

(30) Foreign Application Priority Data

Jul. 8, 1995 (JP) ............................................. 7-196035

(51) Int. Cl.7 .................................................. A61F 7/00
(52) U.S. Cl. ............... 607/96; 126/263.02; 126/263.05; 126/263.07; 428/34.3; 428/35.2; 428/35.7; 604/20; 604/108; 604/113; 604/114; 604/291; 607/104; 607/108; 607/111; 607/114

(58) Field of Search .................................. 604/108, 114, 604/20, 113, 291; 607/111, 114, 104, 108, 96; 126/263.02, 263.05, 263.07; 428/34.3, 35.2, 35.7

(56) References Cited

U.S. PATENT DOCUMENTS

| | | | | | |
|---|---|---|---|---|---|
| 3,903,011 | A | * | 9/1975 | Donnelly | 252/188.3 R |
| 4,203,418 | A | * | 5/1980 | Donnelly | 126/263 |
| 4,268,272 | A | * | 5/1981 | Taura | 126/204 |
| RE32,026 | E | * | 11/1985 | Yamashita et al. | 126/263 |
| 4,649,895 | A | * | 3/1987 | Yasuki et al. | 126/263 |
| 5,277,180 | A | * | 1/1994 | Angelillo et al. | 607/114 |
| 5,879,378 | A | * | 3/1999 | Usui | 607/96 |

FOREIGN PATENT DOCUMENTS

JP 56020450 * 2/1981

* cited by examiner

Primary Examiner—Judy M. Reddick
(74) Attorney, Agent, or Firm—Ronald E. Greigg

(57) ABSTRACT

The present invention relating to an exothermic decomposition has, as essential components, a water absorptive polymer and/or tackifier, carbon component and/or metal chloride and features that the product is as a whole ink-like or cream-like.

21 Claims, 3 Drawing Sheets

INK LIKE OR CREAM-LIKE EXOTHERMIC COMPOSITION, EXOTHERMIC DEVICE MADE THEREOF AND MANUFACTURING METHOD OF EXOTHERMIC DEVICE

BACKGROUND OF THE INVENTION

1. Field of the Invention

The present invention relates to formation of a range of fluid exothermic compositions and of having these enclosed in what are known generally as pouches by such a transfer, which now enable high-speed manufacture of ultra-thin filled pouches, the filled composition being uniformly distributable, and each of such exothermic pouches being thin, soft and flexible and excelled in touch in use because of the fluid feature of, e.g., the transferred exothermic composition which can be packed in a mating bag partly or entirely fixed thereto, and the invention also relates thereto.

2. Description of the Related Art

In recent years, disposable flat body warmers such as exothermic devices having an exothermic composition enclosed in a flat pouch made of a gas-permeable or gas-tight filmy or thin covering material are widely in use.

Some disposable body warmers have an adhesive layer formed on one surface thereof to be applied directly or through underwear to the skin and also proposals have been made having a wet compress agent contained or carried therein for use as a wet compress or having a medication contained or carried therein for use as a skin absorbable medication (see Japanese Patent laid-open Publication No. 2-149272).

As a manufacturing method for such exothermic devices, generally adopted are such methods as having a given exothermic composition deposited in a given region of the substrate and a gas-permeable cover placed thereon. This is followed by sealing the edges by heat-sealing or bondage by the use of a hot-melt adhesive.

Exothermic devices thus manufactured have the exothermic reaction inhibited before use, hence the exothermic composition is in the gas-tight outer bag as they are stored or distributed.

As conventional exothermic compositions were known, besides metal powder and water essential for an exothermic reaction, carbon components such as carbon or active carbon are known for enhancing the exothermic reaction, metal halides for successive progress of the exothermic reaction through destruction of a surface oxide film of metal powder and further water-retainers such as wood flour.

As a method of depositing the powdery composition, there are known alternative methods of moving the substrate intermittently and depositing the powdery exothermic composition when the substrate is stopped and moving the exothermic composition discharging port at the same speed as the substrate to deposit the powdery exothermic composition on the moving substrate. For enhancing the manufacture, however, the latter method is preferred.

When the exothermic composition is formed powdery as in the past, the powdery exothermic composition is compounded in an optimum state such that the exothermic reaction, namely the oxidation reaction, is likely to occur. Moreover, it is powdery and highly porous, high in specific surface area and is extremely good in contact with air, thus causing immediate starting of an oxidation reaction upon contact with air.

If an oxidative reaction with air, i.e., exothermic reaction, should take place during compounding exothermic compositions at a proper ratio and during the period between manufacture of the exothermic compositions and completion of manufacture of the exothermic device, this resulting in loss due to an exothermic reaction of an exothermic composition as well as lowering of the quality of the exothermic compositions and giving rise to various problems such as coagulation of compositions resulting from the exothermic reaction. Specifically, lowering yield due to removal of coagulants, increased difficulty in handling, growing complications of machine maintenance, more strict limitation of a machine's per-day operating hours and a worker's working hours, increased difficulty of treatment or disposal of coagulants.

If the exothermic composition is powdery, oxidation reaction with air takes place after manufacture of an exothermic device and before sealing the resulting exothermic device in the gas-tight outer pouch, this resulting in fatal defects such as lowering of the quality of an exothermic device as well as of its reliability.

For prevention of an oxidation reaction of such exothermic compositions, it is possible to make the mixer gas-tight and replace the air with nitrogen before proceeding to uniform mixing of the exothermic compositions. This way, however, the mixer not only becomes more complicated and more expensive, this also results in increased costs of the exothermic compositions and exothermic devices, Another method of depositing the exothermic composition when the substrate is stopped in the course of its intermittent movement has a drawback of the manufacturing speed getting lower, for the substrate stops and restarts frequently.

Still another method of depositing the exothermic composition onto the substrate moving at a constant speed through the deposition port being moved at the same speed enables increasing the manufacturing speed because the substrate is seldom stopped and restarted.

Since, in this case, a complicated mechanism becomes necessary for moving the deposition part for the exothermic composition at the same speed as the substrate and, worse, the exothermic composition is moistened by addition of water and, being powdery, is less frequent, there are many problems such as a strict limit for the speed of moving the mechanism, decreased reliability due to poor filling property of the exothermic composition, increased scatter of the filling rate of the exothermic composition and eccentricity of the exothermic composition in the pouch.

Although the exothermic composition is moistened by addition of water, the water content is low and proper for exothermic reaction, hence it is powdery and less liquid and it is extremely difficult to have it uniformly distributed in a predetermined region of the substrate.

Although the distribution of the exothermic composition is not uniform to some extent by, e.g., a roller as it is sealed with a covering material thereon, the distribution of the exothermic composition tends to be shifted toward a direction from which the pouch is sent. Hence, in order to increase the distribution of the exothermic composition where the porches are sent, it is necessary to make the exothermic device thicker and eliminate distribution error by shaking it by hand before use.

Hence, the exothermic devices as a whole become thicker to several mm, its feel becomes stiff and disagreeable and, worse, its softness is deteriorated with an increasing difficulty to fit the complicated curvature of the body surface with failure to fit small curvatures. Also deteriorated are prolongation and stretching behaviors, this resulting in failure to readily follow movement of the body surface and giving problems of an increased stiff feel, unpleasant feel or the like.

In order to put an exothermic device in a shoe to produce warmth, it is essential to try to have it thinner but in this respect the conventional exothermic devices which are several mm thick are by far unsatisfactory.

Especially the conventional disposable body warmers, which have filled therein powdery exothermic composition, are not constant in thickness with the exothermic composition shifting therein and, when some thereof is immovably fixed to the body surface, non-constant distribution of exothermic temperature can possibly cause a burn.

In recent years, popularized products have been arranged to prevent off-center displacement in any direction but to date there has been established no measure against displacement in any direction in any of the manufacturing processes, transport stage and distribution stage.

When the exothermic composition is stored in an outer pouch (storage pouch), the exothermic device has its inside undecompressed and in the transfer stage the exothermic composition is movable or shiftable in the exothermic device. Also for ensuring safety, it is important to have the pouch's thickness kept uniform and have the temperature distribution constant and with those having the exothermic decomposition shifted off-center it is a current practice to be returned as unfit products in the distribution stage or exchanged when the consumer demands. Thus it is extremely important to ensure uniformity of thickness of the exothermic composition in the transport stage.

In Japanese Patent Laid-Open Publication No. 62-347 there is proposed a method of fixing an exothermic composition by an adhesive. In practical manufacture, however, it is almost impossible to bond a powdery exothermic composition to the inside of the exothermic pouch and, even if it is feasible, the bonding strength is lowered and perfect fixing is not feasible, the exothermic device is subject to separation or becomes plate-like in a user's feel. Worse, coexistence of an adhesive agent interferes with contact between the exothermic composition and air, this resulting in temperature unevenness and scattering of temperature, and lack of utility.

Hence, in order to solve the above-noted technical problems, the inventor has made intensive studies about exothermic devices for prevention of various problems such as loss of the exothermic composition due to exothermic reaction at the time of manufacture, lowering the quality of the exothermic composition and coagulation thereof to thereby enable high-speed manufacture of ultra-thin exothermic devices, also having such additional features as prevention of movement and off-center displacement of the exothermic composition by distribution thereof in the pouch and fixing therein and preclusion of excessive exothermic reaction of the exothermic composition as far as possible.

As the result, it turned out that the exothermic principle of disposable body warmers is generation of heat taking place when metal powder is oxidized and that this oxidation reaction, namely, an exothermic reaction, has its reaction time largely dependent upon the presence of water.

In order to enhance this exothermic reaction, quite important is the presence of proper moisture, not too high or too low degree thereof which markedly retards such a reaction. The presence of proper moisture enables balancing of water with air (oxygen) supply to metal powder to thereby enable progress of the oxidation reaction, namely, exothermic reaction, at the highest reaction time.

Too little water results in shortage of water required for a reaction in the presence of ample air, while too much water retards the reaction with the excessive moisture forming a barrier against a supply of air to metal powder.

Through such studies the inventor discovered that ultra-thin exothermic devices are extremely easy to laminate by screen printing, coating or the like and can be manufactured at high production when the exothermic composition is prepared to be fluid.

The inventor also discovered that such thickened exothermic composition can be uniformly distributed in the pouch and that when the fluid exothermic composition is laminated on paper including thin paper for household use such as a foamed film sheet, tissue paper and towel paper and thick papers such as cardboard and corrugating medium thereof (hereinafter referred to as papers), nonwoven fabric, woven cloth or a porous film sheet, this fluid exothermic composition with its high penetration and anchoring capability gets into the pores of such film or sheet to be safe from movement or displacement in any direction thereafter.

Further, the inventor discovered that, especially when such film or sheet has water-absorbency and the exothermic composition is laminated thereon or when a water-absorptive layer is formed on the above-noted film or sheet and the fluid exothermic composition is laminated thereon, a whole or a part of the exothermic composition becomes more readily and securely fixed to the forming film or sheet, papers, nonwoven fabric, woven cloth or porous film or sheet or the water-absorptive layer formed thereon and thus its later movement or displacement in any direction is precluded.

The inventor also discovered that, when the exothermic composition is formed as a fluid, the surface area becomes markedly less than that of the powdery exothermic composition, this resulting in strict limitation of contact with air and marked suppression of the oxidation reaction with air.

Further, the inventor discovered that in the fluid exothermic composition excessive moisture or free moisture and/or water-containing gel covers the metal powder and forms an air barrier layer, this, too, resulting in extreme stability of the exothermic composition in the air.

In this case, where water is excessively incorporated in the exothermic composition, as in the case of fluid exothermic composition, the excessive moisture functions as a barrier layer, this further suppresses the exothermic reaction (oxidation reaction) with air and contributes to further improvement of stability.

Meanwhile, in the fluid exothermic composition it is not absolutely necessary to incorporate water excessively and relatively less water content will do as in the case of the fluid exothermic composition. In such a case free moisture and/or water-containing gel (water-containing) covers the metal powder and functions as a gas-barrier layer, hence its stability in the air is improved.

As in the case of a deoxidant containing an excessive amount of water, excessive moisture is absorbed by at least one of the backing, covering materials and water-absorptive materials applied to either or both sides of the fluid exothermic composition. In the case of the fluid exothermic composition, too, a part of free moisture and/or water-containing gel is absorbed by at least one of the backing, covering material or water-absorptive material applied to either or both sides of the fluid exothermic, this resulting in loss of the barrier, and the exothermic composition, now porous, is in good contact with air and the exothermic reaction proceeds smoothly.

Therefore, there is scarcely any oxidation reaction, namely exothermic reaction, during compounding of the exothermic composition and in the steps of manufacture of fluid exothermic composition, lamination thereof on the substrate by printing, coating or the like and manufacture of exothermic devices by covering the laminate with a proper material, hence loss of the exothermic composition with progress of an exothermic reaction and deterioration of the quality of the exothermic composition and coagulation of the exothermic composition is precluded. Hence, the reaction yield and handling behavior are improved, machine maintenance became easy and limitations about machine's per-day working hours and worker's working hours were totally removed.

When the exothermic composition is fluid, there can scarcely be any oxidation reaction with air in the course of manufacture of exothermic devices until sealing thereof in a gas-tight outer pouch, hence the quality of the exothermic device is stabilized and its reliability is improved.

Thus, the inventor discovered that, since the fluid exothermic composition is stabilized in the air, it is not necessary to make the mixer gas-tight and it is neither necessary to replace air in the mixer with nitrogen, hence a simple mixer is enough and the exothermic composition and exothermic device can be manufactured at low costs.

When, as mentioned above, the exothermic composition used is fluid, screen printing or transfer and lamination by coating or the like are extremely easy and ultra-thin exothermic devices can be manufactured at a high output. Moreover, the exothermic composition can be distributed inside a pouch uniformly, and movement and displacement in any direction of the exothermic composition during use or handling can be prevented.

The inventor discovered that the exothermic device can be made extremely thin by printing such as screen printing or by a lamination method such as coating and, further, since the per-hour exothermic reaction rate is lowered as the exothermic device is made thinner, excessive exothermic reaction of the exothermic device can be precluded.

The inventor discovered that by having an aqueous viscous solution of a water absorber laminated on a pouch of foam film, sheet, paper, nonwoven fabric or porous film or sheet by impregnation, scattering, kneading, printing, coating or the like and subsequent drying or by first imparting water absorbency by having a water absorber contained in or carried by the pouch by pressing, kneading or the like and then having the fluid exothermic composition transferred or laminated thereon by screen printing, coating or the like. This way, the step of throwing-in powder can be eliminated and the plant control meeting the GMP standards to be applied in the near future to manufacture of medical instruments and medicines will become readily feasible.

The inventor also discovered that when the excessive moisture or free moisture or a part of water in a water-containing gel is absorbed by at least one of the water-absorbing materials is applied to either or both sides of the fluid exothermic composition, the barrier layer is eliminated and at the time of use, the exothermic composition is porous and in good contact with air, thus resulting in excellent exothermic properties.

The present invention has been completed on the basis of the technical knowledge described above, and is aimed at preventing generation of dust in the course of manufacture of exothermic devices, at eliminating loss due to exothermic reaction and precluding lowering of the quality of the exothermic composition and coagulation of the exothermic composition, uniform distribution of the exothermic composition through adoption of printing and transferring methods such as screen printing and coating, attaining a high precision of measuring the thickness and distribution of the exothermic composition for accomplishing an improved quality of the product and also facilitating high-speed manufacture of ultra-thin exothermic devices, transfer and lamination of the exothermic composition on water absorptive substrate or covering material or on a water-absorbing layer for uniform distribution and fixing of the exothermic composition and also for ensuring against movement and displacement in any direction of the exothermic composition.

Another object of this invention is to make a pouch water-absorptive with a viscous aqueous solution of a water absorber by impregnation, spraying, kneading, printing or coating (lamination) and subsequent drying or with a water absorber by pressing or kneading to be contained therein or carried thereby, this followed by transfer or lamination of an exothermic composition, this allowing elimination of the step of throwing-in powder and plant control meeting GMP standards to be applied in the near future to manufacture of medical instruments and medicines will become readily feasible.

SUMMARY OF THE INVENTION

The fluid exothermic composition according to the present invention (hereinafter referred to as invented composition) features, for accomplishment of the above-described objects, having an exothermic substance, water-absorptive polymer and/or tackifier, carbon component and/or metal halide and water as essential components, and features to be generally fluid.

The exothermic device of the invention (hereinafter referred to as invented exothermic device) is, for accomplishment of the above-described object, made up of the invented composition laminated and sealed in a thin pouch, at least part of the pouch is gas-permeable and a part of water of the invented composition noted above is absorbed by the aforementioned thin pouch.

The manufacturing method for the first exothermic device of the invention (hereinafter referred to as invented method for the first exothermic device) comprises, for accomplishment of the above-described object, the steps of preparing a fluid exothermic composition, laminating the fluid exothermic composition on at least a part of a film of or a thin sheet of substrate, placing a film of or a thin sheet of covering material so as to cover said fluid exothermic composition. At least, either the substrate or the covering material or a part thereof is gas-permeable.

The manufacturing method for the second exothermic device of the invention (hereinafter referred to as invented method for the second exothermic device) comprises, for accomplishment of the above-described object, the steps of preparing a fluid exothermic composition, laminating the fluid exothermic composition on at least a part of a film of or a thin sheet of substrate, laminating or scattering at least one component selected from the group consisting of an iron powder, a carbon component and a water absorptive agent on a surface of the fluid exothermic composition, placing a film of or a thin sheet of covering material so as to cover the fluid exothermic composition and the selected component. At least either the substrate or the covering material or a part thereof is gas-permeable.

The manufacturing method for the third exothermic device of the invention (hereinafter referred to as invented method for the third exothermic device) comprises, for accomplishment of the above-described object, the steps of preparing a fluid exothermic composition, laminating the fluid exothermic composition on a film of or a thin sheet of substrate, placing a film of or a thin sheet of covering material so as to cover the fluid exothermic composition, putting together the substrate and the covering material to obtain a laminae by a viscosity of the fluid exothermic composition, and stamping out the laminate into a predetermined shape. At least either the substrate or the covering material or a part thereof is gas-permeable.

Hereinafter the invented composition, the invented exothermic device and the invented methods 1 to 3 will be described in detail.

The invented composition here is not meant to be a conventional powdery one but an exothermic composition made as a fluid.

Further, this invented composition is composed of components capable of entering into exothermic reaction with oxygen in the air, and there is no particular limitation as long as it is a fluid and changes shape when subjected to an external force.

Specifically, the invented composition is obtainable through adjustment of the mixing ratios for water, water-absorptive polymer and/or tackifier and other components.

The invented composition is formed as a fluid, this accounting for the various advantages described below.

Since the invented composition is fluid, printing is feasible by many known methods such as thick-film printing, gravure printing, offset printing, screen printing and spray printing, transfer or lamination is readily feasible by the use of a head coater, a roller or an applicator, ultra-thin invented exothermic devices may as well be manufactured at a high speed, readily transferrable and laminatable and, further, it is possible to have the invented composition uniformly distributed in a pouch.

When this invented composition is transferred or laminated onto a foam film or sheet, paper, nonwoven or woven fabric or porous film or sheet, this invented composition being fluid has a high penetrating and anchoring capability and gets into pores of the film or sheet to stay there and is no longer movable or displaceable; the specific area of contact with air is extremely small and with the air supply diminished, penetration and anchoring capability gets into the pores of the film or sheet to be restricted from movement or displacement, the area for contact with air is extremely small and the air supply is thus diminished, there is scarcely any chance for progress of oxidation reaction.

In such a case, especially where such film or sheet is absorbent and the invented composition is laminated thereon, the same is done after forming a water-absorptive layer, hence the whole or a part of the exothermic composition is more securely held by the foam film or sheet, paper, nonwoven fabric or porous film or sheet and also by the water-absorbent layer, this resulting in less chance for removal or displacing of such coating. When lamination is made by screen printing or coating, this exothermic composition can be made extremely thin and since the per-hour exothermic reaction rate decreases with decreasing thickness of the exothermic device, excessive progress of the exothermic reaction is retarded, but, since the invented composition is fluid and the coated thickness is small, removal or displacement of the formed exothermic coating is hardly feasible.

When the viscous aqueous solution of water absorber is laminated on a pouch of foam film or sheet, paper, nonwoven fabric, woven cloth or porous film or sheet by impregnation, spraying, printing or coating (lamination) and subsequent drying or by pressing or kneading a water-absorber to have it contained in or carried by a pouch of sheet, this is followed by transfer or lamination of the invented composition, this allowing elimination of the step of throwing-in powder and plant control meeting GMP standards to be applied in the near future to manufacture of medical instruments and medicines will become readily feasible. As the above-noted water absorber is mainly used, a water-absorptive polymer or tackifier will be described later.

Since the invented composition is fluid with the water content of the exothermic composition and with the ratios of water-absorptive polymer, and/or tackifier properly adjusted, transfer or lamination by printing or coating is extremely easy and manufacture of ultra-thin exothermic device can be made at a high speed. Moreover, since the excessive moisture acts as barrier, the air feeding rate decreases until substantial stopping of the exothermic reaction, this resulting in further stabilization of moisture in the air, which is preferred for reduced loss by exothermic reaction at the time of manufacture and also for increased safety from deterioration of the exothermic composition as well as from coagulation thereof.

In this case, when the excessive moisture or free moisture or a part of water in the water-containing gel is absorbed by the pouch material, i.e., substrate and/or covering sheet, loss of the barrier layers results, a further merit being absorption of water by the pouch and the resultant increased porousness of the invented composition, which enhances contact with air.

In the invented exothermic composition, when the exothermic substance with water-absorbing polymer and/or tackifier, carbon content and/or metal halide and water as essential components has its viscosity adjusted to be fluid, the composition being: water-absorptive polymer in 0.1 to 7.5 parts by weight and/or tackifier by weight in 0.1 to 10 parts and carbon component in 1.5 to 20 in parts by weight and/or metal chloride in 1 to 10 parts by weight as essential components per 100 in parts by weight, there mixed with further addition of water for the whole to be fluid.

In this case, for preparation of the invented composition, the solid components alone are thrown into a mixer and after uniformly mixing them, water and/or aqueous solution of the metal halide may be added for preparation of a fluid liquid or alternatively all of these exothermic components may be mixed in the mixer to produce a fluid.

In case that water is in excess, there is no particular limitation about the mixer for such components as long as it is capable of uniform mixing but in the case of a fluid exothermic composition with a relatively less water content, the kneading apparatus such as a kneader or mixer is preferred for the case of a fluid formation of exothermic composition and, moreover, the surface of the exothermic composition is easily covered by free moisture or water-containing gel.

As mentioned above, the invented exothermic composition is formed as a fluid but it is desirable to have its viscosity (at 20° C.) measured by the method described below generally in a range of 1,000 to 7,500,000 cps, for if it is less than 1,000 cps, there results deterioration of transferability of the exothermic composition such as printing or coating, extreme excess of water resulting in shortage of the quantities transferable of other components, whereby the time of exothermic reaction is shortened due to extreme excess of water, this resulting in shortage of transferable quantities of other components, oozing of the exothermic composition beyond the predetermined region on the substrate or necessity of having a large amount of water absorbed by the substrate and the like, this, in turn, resulting in the necessity of using a substrate etc. of special structure or of complicating the structure of the exothermic composition, while, if it is in excess of 7,500,000 cps, it is not preferable, either, for deterioration of transferability causing scatter of transferred quantities or possibility of the exothermic reaction taking place in the surface. For these reasons, it is preferable to have this range from about 1,000 to about 6,500,000 cps, more preferably from about 50,000 to 5,500,000 cps.

By viscosity it is here meant, when it is less than 2,000,000 cps., the value measured at 20° C. by the use of a viscosimeter BH-type (manufactured by TOKIMEC INC.), a #7 rotor (2 rpm.) and a beaker (85φ) in inside diameter), and if it is in excess of 2,000,000 cps., is a value measured at 20° C. by the use of a R110-type viscosimeter (RE110U system, Detection Head RE100U Controller RC100A, manufactured by Toki Sangyo K. K.) and an SPP rotor 0.2 rpm (D=0.4 (1/S)).

The viscosity is here meant a value of what is transferred or laminated.

The components of the invented composition include, besides exothermic materials essential for exothermic reaction, namely water, water-absorptive polymer and/or tackifier and the like, carbon components such as carbon and active carbon for enhancing generation of heat and/or metal halide for destruction of the superficial oxide film of metal powder and successive occurrence of the exothermic reaction and, besides such essential components, inorganic or organic water retainer, pH adjuster, surface active agents for enhancing dispersibility, defoaming agent, etc. are added, as desired.

The compounding ratio of the invented composition, although it depends on the kind of the water-absorptive polymer and tackifier, the kind of exothermic materials and carbon components and the kind of metal halide, it is generally preferred to be in 0.1 to 7.5 parts by weight of water-absorptive polymer, in 0.1 to 10 parts by weight of tackifier, in 1.5 to 20 parts by weight of carbon component and in 1 to 10 parts by weight of metal halide, and water is added to this mixture to make the whole a fluid. In this case, the required quantity of metal halide is dissolved or dispersed in water and adding the same to a mixture of water-adsorptive polymer and/or tackifier and carbon components and/or metal halide for the whole to be fluid.

In this case, instead of adding water or an aqueous solution or aqueous dispersion of metal halide, it is possible to add proper amount of water to the aforementioned solid components and uniformly mixing the whole for preparation of a product of the invented composition.

In this case, too, as in the previous case, it is preferred to have its viscosity (20° C.) generally in a range of 1,000 to 7,500,000 cps. as measured by the method described above.

In the invented composition, as mentioned above, the desired exothermic property is obtainable even if it is composed of water, water-adsorptive polymer and/or tackifier, exothermic substance, carbon components and metal halide but, improvement of further temperature stability and lengthening of the time of exothermic reaction it is preferable to further add inorganic or organic water-retainer, pH adjuster, surface active agents for improving dispersibility and defoaming agents for making the whole a fluid.

That is, the exothermic composition includes 0.1 to 7.5 parts by weight of water-absorptive polymer and/or 0.1 to 10 parts by weight of metal halide per 100 parts by weight of exothermic substance. Mixed in 100 parts by weight of this exothermic composition are at least one of 0.5 to 10 parts by weight of inorganic or organic water-retainer, 0.1 to 5 parts by weight of pH adjuster, 0.1 to 5 parts by weight of surface active agent for improving dispersibility, and 0.1 to 5 parts by weight of defoaming agent. In the present invention, water is added to this mixture so that the exothermic composition becomes a fluid. Of these, most preferred is metal halide, the required quantity of which may be dissolved or dispersed in water, added to the aforementioned mixture and the whole is made fluid, this being particularly excellent in exothermic property. Thus, instead of mixing the solid components uniformly and then adding water, aqueous solution or dispersion of metal halide, a proper amount of water may as well be added to the aforementioned solid components and the invented composition is obtainable by uniform mixing.

In this case, too, as in the above-described case, the invented composition is generally preferred to be 1,000 to 7,500,000 cps. in viscosity (20° C.) as measured by the above described method.

In the invented composition, the cited water-absorptive polymers are high polymers capable of absorbing a large amount of water or aqueous solution of metal halide smoothly, specific examples thereof being one or a combination of two or more of starch-polyacrylonitrile copolymer disclosed in Japanese Patent Publication No. 49-43395, crosslinked polyalkylene oxide disclosed in Japanese Patent Publication No. 51-39672, vinylester-ethylene-type unsaturated carboxylic copolymer saponificate disclosed in Japanese Patent Publication No. 53-13495, self-crosslinked polyacrylic salt obtained by reverse phase suspension polymerization disclosed in Japanese Patent Publication No. 54-30710, a reaction product of polyvinyl alcohol polymer and cyclic anhydride disclosed in Japanese Patent Laid-Open Publication No. 54-20093, polyacrylic salt crosslinked compound disclosed in Japanese Patent Laid-Open Publication No. 59-84305, N-vinylacetoamide crosslinked compound (water-absorber having a water-absorptive ability) (NA-010 manufactured by Showa Denko K. K.). These may further be treated with a surface active agent and it is also possible to add surfactant thereto for improved hydrophilic property. Some of these hydrophilic polymers are capable of absorbing water or aqueous solution of metal halide for imparting viscosity but they mainly have a function of absorbing a large amount of water or aqueous solution of metal halide smoothly.

A commercially available product may be used as a water absorptive polymer. Examples thereof include Sanwet IM-300, Sanwet IM-300 MPS, Sanwet IM-1000, Sanwet IM-1000MPS, Sanwet IM-5000 and Sanwet IM-5000MPS manufactured by Sanyo Kasei K. K., Aquakeep 4S and Aquakeep 4SH manufactured by Seitetsu Kagaku K. K., Sumikagel NP-1020, Sumikagel NP-1040, Sumikagel SP-520 and Sumikagel N-1040 manufactured by Sumitomo Kagaku K. K., KI Gel 201-K and KI Gel 201-F2 manufactured by Kurare K. K., and Arasoap 800 and Arasoap 800F manufactured by Arakawa Kagaku K. K.

Of such commercially available water-adsorptive polymers, particularly preferred are Sanyo Kasei K. K.'s Sanwet IM-300MPS, Sanwet IM-1000MPS and Sanwet IM-5000MPS, Sumitomo Kagaku K. K.'s Sumikagel NP-1020 and Sumikagel NP-1040, Kurare K. K.'s KI Gel 201-K and KI Gel 201-F2 and Arakawa Kagaku K. K.'s Arasoap 800F.

As tackifiers for the invented composition are mainly used substances absorbing water or aqueous solution of metal halide for increasing their consistency or imparting thixotropy such as bentonite, polyacrylate such as stearates and sodium polyacrylate, gelatin, polyethylene oxide, polyvinyl alcohol, polyvinyl pyrrolidone, gum arabic tragacanth gum, locust bean gum, gua gum, alginates such as sodium alginate, pectin, carboxyl vinyl polymer, dextrin, a-starch, starch flour-type water absorber such as starch flour for processing, carrageenan, polysaccharide-type tackifiers such as agar, CMC, cellulose-derivative-type tackifiers such as ethyl cellulose acetate, hydroxy ethyl cellulose or hydroxy propyl cellulose, acryl sulfonic acid-type high-polymers (such as CS-6HS manufactured by Nippon Shokubai K. K.), water-soluble cellulose ether and poly-N-vinyl acetamide, either alone or in combination of two or more. These are also treated with a surface active agent or mixed therewith for improvement in hydrophilic property. Such tackifiers are used mainly for absorbing water or aqueous solution of metal halide for increasing consistency or imparting thixotropy.

As specific examples of the aforementioned cellulose ethers may be cited methyl cellulose with cellulose etherified with methoxyl group (such as Metrose SM15, Metrose SM25, Metrose SM400 and Metrose SM4,000 manufactured by Shin'etsu Kagaku Kogyo K. K.), hydrozy propyl methyl cellulose with cellulose etherified with hydroxy propoxyl group (such as Metrose 60SH-50, Metrose 60SH4,000, Metrose 90SH4,000, Metrose 90SH-30,000, Metrose 90SH-100,000 of Shin'etsu Kagaku Kogyo K. K.), water-soluble cellulose ether like hydroxyethylmethyl cellulose ether with the cellulose contained etherified by hydroxyethoxyl group (such as Metrose 60SH-50, Metrose 60SH-4,000, Metrose 90SH-4,000, Metrose 90SH-30,000, Metrose 90SH-100,000) and water soluble cellulose ethers such as Cerogen EP, Cerogen BSH-12, Sesuka MC, Sesuka MHEC abd Sesuka MHPC manufactured by Daiichi Kogyo Seiyaku K. K.

When an aqueous solution of this water-soluble cellulose either is heated to a predetermined temperature (tackiness-induced temperature), it results in increase of viscosity, but if heating is continued beyond this temperature, release of adsorbed water causes gelation (hereinafter called as phenomenon of tackiness-induced gelation), this resulting in releasing of water for formation of a moisture barrier for inhibiting the exothermic reaction, while, if the formed gel is cooled, the initial state is restored through adsorption of water.

The tackiness-induced temperature of water-soluble cellulose either depends on the kind of the etherifier, substitution ratio, the molecular weight of the cellulose, the concentration of the solution when it is added as solution, the kind and amount added (concentration) of any other additive, if any, and also heating/cooling rates. Hence, when water-soluble cellulose ether is used as a tackifier, the maximum exothermic temperature can be properly determined through proper action of the kind of the etherifier used, the substitution ratio, the molecular weight of the cellulose, the solution's concentration and the kinds and dosages (concentrations) of other additives for controlling the heating and cooling rates.

With 2% by weight of aqueous solution of, for example, the aforementioned water-soluble cellulose either (Metrose SM4000 manufactured by Shin'etsu Kagaku Kogyo K. K.) the tackiness-induced temperature is 55° C. in the case of no additive, the tackiness-induced temperature is lowered to 40° C. when 5% by weight of sodium chloride (NaCl) or sodium carbonate (Na2CO3.10H20) is added, hence, in the case of direct application to the human body, Metrose SM4000 release the adsorbed water below the safety temperature (43° C.) for suppressing the exothermic reaction.

The tackiness-induced temperature of this Metrose SM4000 is 45° C. when 5% by weight of Al2(SO4)3.18H2O is added, and at this temperature Metrose SM4000 releases the adsorbed water around the metal powder to suppress the exothermic reaction.

With 2% by weight of aqueous solution of, for example, water-soluble cellulose ether (Metrose 60SH-4000 manufactured by Shin'etsu Kagaku Kogyo K. K.), the tackiness-induced temperature is 75° C. in the case of no additive. The tackiness-induced temperature is lowered to 70° C. when 5% by weight of sodium chloride NaCl). The tackiness-induced temperature is lowered to 45° C. when 5% by weight of sodium carbonate (Na2CO3.10H2O). At these temperatures Metrose 60SH-4000 releases the adsorbed water around the metal powder to suppress the exothermic reaction.

The tackiness-induced temperature of Metrose 60SH-4000 is lowered to 50° C. when 5% by weight of $Al_2(SO_4)_3 18H_2O$ is added and at this temperature Metrose 60SH-4000 releases the adsorbed water for increasing the quantity of free moisture around the metal powder to suppress the exothermic reaction.

Examples for additives for adjusting the tackiness-induced temperature of the aforementioned tackifiers include inorganic compounds and hydrates such as sodium chloride, sodium carbonate and aluminum sulfate, lower alcohols such as ethanol, polyhydric alcohols such as polyethylene glycol and glycerin and also the aforementioned water-absorptive polymer and tackifiers.

The aforementioned poly-N-vinylacetoamide is obtainable by radical polymerization of N-vinylacetoamide and there are known two categories, one being of water-soluble direct chain structure and the other being of water-insoluble crosslinked structure. The water-insoluble poly-N-vinylacetoamide includes microgel which functions as gelatinizer because of the difference in crosslinking density, specifically N-vinylacetoamide-sodium acrylate copolymer (GE-167 manufactured by Showa Denko K. K.), N-vinylacetoamide homopolymer (GE-191 manufactured by Showa Denko K. K.) and N-vinylacetoamide crosslinked (microgel) (GX-205 manufactured by Showa Denko K. K.) used alone or in combination of two or more. Further, these can be treated with some surfactant or combined therewith for improved hydrophilic property. These tackifiers have a principal function of absorbing water or aqueous solution of metal halide for increasing consistency or imparting thixotropy.

For the invented composition organic matters are usable as an exothermic substance, but generally iron powder, zinc powder, aluminum powder or magnesium powder or pulverized alloy of two or more of these metals free from generating odor but most preferred is iron powder with its safety, ease of handling, cost, storage property and stability.

As carbon components carbon black, graphite or active carbon are cited and as metal halides cited are chlorides of alkali metals such as sodium chloride and potassium chloride and chlorides of alkaline earth metals such as calcium chloride and magnesium chloride.

The aforementioned inorganic or organic water retainers not only release the retained water when the water present in the exothermic composition is insufficient and the exothermic reaction is slackened, but also by improves the percentage of voids in the exothermic composition for improving the chance of contract between air and the exothermic composition.

Specifically cited are such as pearlite, cristobalite, vermiculite, silicates such as calcium silicate, quartzite, silica-type porous substances silicates such as calcium silicate fluorite, diatomaceous earth, alumina, alumina silicate such as mica powder and clay, magnesia silicate such as talc, silica powder, wooden flour and pulp powder.

As the aforementioned pH adjusters, surfactants and defoaming agents are used, besides ordinary pH adjusters such as sodium polyphosphate and many others in common use in this field.

With the invented composition, it is advisable to have a part of the water absorbed by the substrate and/or covering material to thereby improve contact with the air when it is in use.

Since, as described above, the exothermic composition of the present invention is formed as a fluid, this allowing lamination thereof on a substrate by, e.g., printing, it allows high-precision control of the laminated region and thinness and form of the laminate, this allowing high-speed manufacture of the invented exothermic composition.

Since the invented composition is laminated on the upper surface of the substrate and after covering thereof with a covering material the excessive moisture or free moisture or water in the water-containing gel is absorbed by the substrate and/or the covering material or the water-absorptive layer, there is scarcely any progress of the exothermic reaction of the invented composition, hence loss due to exothermic reaction during manufacture, deterioration of the invented composition or coagulation thereof can be precluded. Moreover, a part of water in the invented composition is absorbed by the substrate and/or the covering material and also the water-absorptive material, hence the distribution of water in the invented composition at the time of use is suited for exothermic reaction, this resulting in good contact with air and possibility of accomplishment of the desired exothermic temperature.

Moreover, as described above, the invented composition with its adhesiveness is laminated on the substrate by printing or coating and is adhered and fixed to the substrate as well as to the covering material or the water-absorptive layer, thereby ensuring against movement of the invented composition in the pouch, against scattering of the temperature thereof and irregular displacement thereof in the pouch for preclusion of occurrence of any high-temperature region and against any risk of low-temperature burn with increased safety in use.

Now the invented exothermic device will be described in detail.

The feature of the invented exothermic device is that the invented composition is laminated and sealed in a thin pouch of sheet material at least part thereof is gas-permeable.

The invented exothermic composition is as cited above and, moreover, it is so arranged that a part of water in the invented composition is absorbed by the aforementioned thin pouch of sheet material.

In the invented exothermic device, the thin pouch of sheet material is made up of a film of sheet substrate and film or sheet covering material and it is desirable that at least either or a part thereof is gas-permeable and water-absorbable.

Although in the invented exothermic device the ultra-thin exothermic device is formed by printing, coating or the like, if the exothermic device is formed thin, decompression due to consumption of oxygen in air by the invented exothermic composition in the pouch is not sufficient for further thinning (to less than 1 mm thick or so) and lightweight feature, and forced attempt thereby results in lowering of per-hour exothermic reaction rate, this possibly interfering with maintenance of the degree of decomposition required to prevent movement and/or displacement in any direction of the invented exothermic composition.

In such a case it is preferable to prevent movement and/or irregular displacement thereof by fixing a whole or a part of the invented exothermic composition to the substrate and/or the covering material.

Specifically, it is possible to form physical irregularity in the surface of the substrate and/or the covering material at least in the region supposed to be in contact with the invented composition or have the substrate and/or the covering material formed of water-absorptive film or sheet and also have physical irregularity formed in the region of contact with the invented composition so as to ensure against movement and/or irregular displacement of the invented composition due to water-absorption-induced adhesion and irregularity-induced resistance.

In the invented composition it is also preferable to have the substrate and/or the covering material of a non-gas-permeable or gas-permeable film or sheet laminated with a water-absorptive material on either or both sides with a surface irregularity so as to ensure against movement and/or irregular displacement of the invented composition due to water-absorption-induced adhesion and irregularity-induced resistance.

That is, although it is desirable that the substrate and/or the covering material are formed of water-absorptive material, there is no limitation if the water-absorptive material is a water-absorptive film or sheet.

There is no particular limitation about the water-absorptive material as long as it has a water-absorbency, regardless of water-absorbency of the raw material.

Specific examples are a foam film or sheet (e.g., water absorptive polyurethane foam) and papers, nonwoven or woven fabrics made of water-absorptive fibers or nonwoven or woven fabrics including water-absorbing fiber, water-absorptive porous films or sheets, foam films or sheets, nonwoven and woven fabrics caused to incorporate or carry a water-absorber by impregnation, kneading or transfer for imparting or enhancing water-absorbency or foam films or sheets, papers, nonwoven or woven fabrics or porous films or sheets regardless of water-absorbency stuck with water-absorptive foam films or sheets, papers, nonwoven or woven fabrics or porous films or sheets cut to the planar size of the invented composition such that the invented composition is in contact therewith.

In the invented exothermic composition it is desirable to have at least part of the substrate and/or the covering material in contact therewith. In this case, the water absorptive layer formed to be in contact with the invented exothermic composition is desired to be easily stuck to the substrate and/or the covering material by sticking, heat-adhesion, or thermofusion along the periphery of the invented composition.

In the invented exothermic composition it is also desirable that the whole or a part of the invented exothermic composition is buried in or bonded to the surface irregularity of the substrate and/or the covering material or the water-absorptive layer thereof for further ensuring against movement or irregular displacement thereof.

Thus, since movement of the invented exothermic composition in the pouch is prevented, irregular displacement and resultant scatter of or abnormal rise of the exothermic temperature can be prevented.

As the aforementioned water-absorptive material may be cited as the above-mentioned water-absorptive polymer and/or a layer of tackifier of the above-mentioned film or sheet of water absorber.

The surface of the substrate and/or the covering material may possibly be flat and smooth but is desirable to have a wetting index of at least 38 dyne and preferably more than 40 dyne for secure bondage with the invented exothermic composition. Hence, where the substrate and/or the covering material has its surface formed of a smooth film or sheet, it is desirable to have its surface roughened by a physical treatment such as corona treatment to thereby raise the wetting index.

When a water-absorptive layer is formed on the substrate and/or the covering material where it comes into contact with the invented exothermic composition, attraction of water into the exothermic composition results in migration into the substrate and/or the covering material and a part thereof to exhibit a powerful anchoring effect in the water-absorptive layer, hence it is not particularly necessary to roughen its surface.

As mentioned above, the substrate and/or the covering material used in the invented exothermic device has the invented exothermic composition generating heat through contact with air as a heat source, hence it is necessary that at least either or a part of the surface of the pouch formed by the substrate and the covering material is gas permeable, but the substrate and/or the covering material is either single layer or multi-layer in the direction of thickness.

In this case, lamination means alternatively overall or partial layer-to-layer jointing by heat-setting, adhesion, gluing and lamination or simple piling of layers followed by heat-sealing or by the use of hot melt adhesive or pressure sensitive adhesive along the periphery or around the center.

In this case, the invented exothermic composition is fluid, hence the exothermic composition can be laminated by high-speed printing, coating or the like and by laminating on the substrate by transfer, printing, gravure printing using a deep-engraved released plate, spray printing or coating is feasible at a high speed of 160 to 200 m/minute or so with a film thickness as small as 0.02 to 1.5 mm in at least one region and with the laminate thickness kept uniform.

In this case, high precision and uniform lamination is made in at least one predetermined region and, moreover, generally thin lamination is feasible in a layer thickness of 0.02 to 1.5 mm or so and preferably 0.1 to 0.5 mm or so, hence manufacture of an ultra-thin invented exothermic device generally 0.5 to 2 mm in overall thickness is obtainable.

In this case, for increased speed of processing, improved precision of control of the deposited region, thinning and uniformization, the substrate may be laminated with the invented exothermic composition with it being paid out from a roll film or roll sheet at a constant speed of, for example, 160 to 200 m/min., this followed by covering with a covering material also being played out from another roll film or roll sheet. In this case, the invented exothermic composition serves a function similar to that of an adhesive for bonding the substrate with the covering material, but it is advisable to have the periphery of the exothermic composition bonded or sealed.

The invented exothermic device is thus having the invented exothermic composition in at least one predetermined region in the upper surface of the thin substrate, this followed by placing the thin covering material over this exothermic composition. In this case, too, the invented exothermic composition plays a function similar to the tackifier. Of course, for further improvement of quality as well as reliability, it is advisable to seal the substrate and the covering material along the periphery by sticking, heat-adhesion or thermofusion.

Where the substrate and/or the covering material is a single layer (single film or sheet), it is desirable, as mentioned above, to roughen its surface if it is smooth in surface or use foam film or sheet, paper, nonwoven or woven fabric or porous film or sheet. When such are of water-soluble material such as water-absorptive fiber, there is no problem, but when the material has no water absorbency, the selected product may be made water-absorbable by incorporating a water-absorptive agent thereinto by soaking, impregnation, transfer or having it carried inside. In this case, if foam film or sheet such as sponge, paper, nonwoven or woven fabric or the like is used, good adhesion with a layer of pressure sensitive adhesive will result as described below. When the substrate is a laminate of two or more films or sheets, see the description already given hereinbefore.

Where the invented exothermic composition is placed between the substrate and the covering material, it may be possible to have at least one of iron powder, carbon component and water absorber (having a water absorptive ability) over the invented exothermic composition laminated on the substrate for enhancing the rise of exothermic temperature in use or for helping control of temperature property. As to amenity control there has been no particular limitation in such cases; there is no particular limitation as long as the temperature property is not aggravated, but generally it is advisable to have it in a range of 1 to 250 g/m$^2$. As the water absorber, the aforementioned water-absorptive polymer or tackifier may be used.

As to the invented exothermic device, it may as well be possible to laminate an upper surface of the invented exothermic composition iron powder coated with carbon component or mixture of iron powder (A) and carbon component (B) and less than 5% by weight of water of the sum of (A) and (B) to thereby present flying of dust during lamination, enhance rise of the exothermic temperature in use and vary the temperature property also in use.

In this case, iron powder is coated with a carbon component by the use of a pressing pressure type mixer, e.g., AM-15F manufactured by Hosokawa Micron K. K., in such a manner that 0.1 to 10 parts by weight of carbon component is added to 100 parts by weight of iron powder and the mixer is operated at a rate of revolution of 500 to 1,500 rpm for 10 to 80 minutes of kneading.

The method of obtaining a mixture of iron powder (A) and carbon component (B) and 5% by weight of the sum of (A) and (B) of water is by the use of AM-15F manufactured by Hosokawa Micron K. K. and generally under conditions of 0.1 to 10 parts by weight of carbon component, 0.3 to 5 parts by weight of water, particularly 0.5 to 3 parts by weight of water, per 100 parts by weight of iron powder, 500 to 1,500 rpm in revolution and 10 to 80 min. in time of kneading. Addition of such a minute amount of water is effective for further prevention of flying dust.

In the invented exothermic device the exothermic composition is laminated on the substrate and in the next step of covering the invented exothermic composition a film or sheet-like water absorbing material precut in the lamination shape, especially thin paper for household use such as blotting paper and tissue paper and also highly water absorbing film or sheet precut in the lamination shape for the invented device were placed on one side of the invented exothermic composition or the invented composition was sandwiched thereby before sealing with the covering material.

In the present invention the method of incorporating a water absorber into in film or sheet comprises having the film or sheet in a solution of the water absorber and waiting for evaporation of the solvent or spraying the water absorber onto the film or sheet, this followed by coating, kneading, pressing, lamination or compounding, interweaving water-absorptive fibers into nonwoven or woven fabrics or blending otherwise.

The aforementioned substrate and/or the covering material are required to have essential mechanical strength such as tensile strength and are preferred to be generally soft and flexible to be well adaptable to the body surface.

With the invented exothermic device, what is important includes improved adaptability to the curved parts, stretching parts and bending parts of the human body and for further adaptability to the stretching parts and bending parts, the substrate and the covering material, i.e., the pouch of the exothermic device, are required to be extensile or, still better, stretchy film or sheet.

That is, the sheet forming the pouch is extensile or, still better, stretchy and is excelled in stretchability. Such exothermic devices are better suited for use on the bending parts, stretching parts and, still better, expanding and contracting parts of the human body like joints in the elbows and knees and, further, in shoulders and arms with retention of excellent adhesion. Still better, there is no feeling of physical disorder or of being sticky in use and in addition to pleasant feeling in use, there is no risk of peeling off in use, being thus highly favorable for users especially with retention of excelled hot compress effect.

As materials of such extensile substrate and covering materials may be cited synthetic resins such as highly extensile polyethylene and polypropylene.

As to extensile substrate and covering material, that is, extensile films or sheets there is no particular limitation as long as the raw material used is extensile but there are many extensile foam films or sheets, nonwoven or woven fabrics and porous films or sheets well combinable with the invented exothermic device; regardless of these having their own water absorptivity, wanted are those made water absorbable by having a water absorber contained therein or thereon or being carried thereby by such methods as impregnation, affixing, kneading, transfer and lamination, and desired is adoption of such improved materials for absorption of water in the invented exothermic device with simultaneous elimination of water barriers for restoring its natural porosity and the original good contact with air.

As raw materials for extensile films or sheets may be cited, for example, natural rubber, synthetic rubber or thermoplastic elastomer. Being highly extensile, these are easy to handle and the thermoplastic elastomer is heat-fusible, thus these are supposed to largely facilitate manufacture of this invented exothermic device.

Of course, the invented exothermic device has nothing to do with whether the substrate and the covering material have stickiness, heat-adhesiveness or thermofusibility, but for further improvement of quality and reliability it is desirable to seal the substrate and the covering material along the periphery of the exothermic composition by sticking, heat-adhesion, or thermofusion.

As the aforementioned synthetic rubbers may be specifically cited, for example, butadiene rubber, isoprene rubber, styrene-butadiene rubber, acrylonitrile-butadiene rubber, chloroprene rubber, isobutylene-isoprene rubber, polyalkylene sulfide, silicone rubber, poly (chlorotri-fluoroethylene), flourinated vinylidene-6-flaunted propylene copolymer, urethane rubber propylene oxide rubber, epichlorohydrine rubber, acrylic ester-acrylonitrile copolymer and acrylic ester-2-chloroethylvinyl ether copolymer.

As the aforementioned thermoplastic elastomers may be specifically cited, for example, olefinic elastomer, polyurethane elastomer and polyester elastomer.

As the aforementioned olefin elastomers may be cited, for example, ethylene-propylene copolymer, ethylene-propylene-diene terpolymer, chlorosulfonated polyethylene, chlorinated polkyethylene and ethylene-vinyl acetate copolymer.

The thickness of the aforementioned substrate and the covering material depend largely on use, specifically being 10 to 5,000 $\mu$m with that for a foot and 10 to 500 $\mu$m, and more preferably 12 to 250 $\mu$m where it is used directly stuck to the human body, being thus generally in a range of 10 to 2,500 $\mu$m and preferably in a range of 12 to 1,000 $\mu$m.

Where the film thickness of the substrate and the covering material is less than 10 $\mu$m, it is not preferable due to possible failure to obtain the necessary mechanical properties and also due to possible difficulty to uniformize the film thickness.

Meanwhile, where the film thickness is in excess of 5,000 $\mu$m, the adaptability to the body surface is markedly lowered even in the case of foam such as sponge and the nature to follow variation or movement of the body surface is lowered and, worse, the feeling to the skin becomes rough or stiff and the thickness of the exothermic device as a whole becomes too large, this being unfavorable.

Hence, it is preferable that the thickness of the substrate is in a range of 10 to 2,500 $\mu$m, and more preferably 12 to 1,000 $\mu$m.

As substrate and/or covering material, foamed or non-foamed films or sheets made of high-polymer materials may be cited but preferred are film or sheet foams, which anchors the invented exothermic composition for more secure prevention of its movement or irregular displacement.

As such high-polymer materials may be cited, for example, polyethylene, polypropylene, polyamide, polyvinyl chloride, polyvinylidene chloride, polyurethane, polystyrene, ethylene-vinyl acetate copolymer saponificate and ethyl-vinyl acetate copolymer.

Where the substrate or the covering material is of laminate type, part thereof may be made of gas-permeable film or sheet. As such gas-permeable film or sheet are used foamed or non-foamed films or sheets, papers, nonwoven or woven fabrics, porous films and sheets, cloths or the like, and as cloths are usable woven, knitted or nonwoven fabrics and the like.

For imparting gas-permeability to a film or sheet made of the aforementioned non-foamed high-polymer materials there are known, besides the method of drawing the film or sheet in the course of its manufacture for formation of airholes or of forming airholes by extraction of specific components, a method of making airholes in the formed film mechanically by, e.g., punching or by the use of needles, and a porous film or sheet is thus obtainable.

Foamed films or sheets made of high-polymer materials have formed therein independent or continuous air bubbles open to both, fore and back, surfaces and there are two alternatives, one pressing the formed film or sheet after foaming for rupture of the dependent or continuous air bubbles for communication to both sides and the other remains gas-tight or not gas-permeable even after foaming.

Papers and cloths like woven, knitted and nonwoven fabrics have structurally formed airholes communicating to both sides, thereby being gas-permeable. As material fibers are usable natural fibers, regenerated fibers made of natural materials such as viscose fiber, semisynthetic fibers and synthetic fibers as well as mixtures of two or more thereof.

As natural fibers are known vegetable fibers such as cotton and linen and animal fibers such as silk and animal hairs. As high-polymer materials constituting synthetic fibers are known, among others, polyethylene, polypropylene, polyamide, polyester, polyvinyl chloride, polyvinylidene chloride, polyurethane, polystyrene, ethylene-vinyl acetate copolymer saponificate and ethylene-vinyl acetate copolymer.

The invented exothermic device is required to have at least one of or a part of the sides or the substrate and the covering material forming its pouch to be gas-permeable.

Where at least either or a part of the substrate and the covering material is gas-permeable, the gas-permeability largely influences the control of the reaction rate or exothermic temperature of the exothermic composition, hence proper control of gas-permeability is preferable for obtaining proper exothermic effect and for ensuring safety through prevention of low-temperature burn. For high-precision control of this gas-permeability, it is preferable to control the gas-permeability of film or sheet by means of water-vapor permeability. Specifically, the water-vapor permeability is to be controlled in a range of 50 to 10,000 g/m$^2$ 24 hr and preferably in a range of 200 to 6,000/m$^2$ 24 hr according to the Lyssy method L80-4000H type.

Where the substrate and/or the covering material is composed of a plurality of gas-permeable films, it is preferable to control the total water-vapor permeability in a range of 50 to 10,000 g/m$^2$ 24 hr also according to the Lyssy method.

When this water-vapor permeability is less than 50 g/m$^2$ 24 hr no sufficient exothermic effect is attainable, while, if it exceeds 10,000 g/m$^2$ 24 hr, the exothermic temperature becomes too high, thereby giving rise to safety problems, or the exothermic time is likely to be too short. Hence, it is particularly preferable to have the water-steam permeability of the gas-permeable film controlled in the range of 100 to 1,000 g/m$^2$ 24 hr whereby safety is ensured and sufficient exothermic effect can be retained over a long time.

A Lyssy method is a method in conformity to the industrial standards in many countries of the world and in JIS Z020 to Z0208 it is determined to keep the relative humidity difference at of 100% RH at the ambient temperature of 40° C. Hence in this apparatus the sample for measurement is inserted between the lower chamber 90% RH and the upper chamber having therein a highly sensitive humidity sensor. The relative humidity in the upper chamber is kept at 10% RH (100%–90%) and with this as the center the time (several seconds) required for rise of humidity from approximately 9% to approximately 11%=approximately ±1% (RH) and the humidity permeability is determined by comparison with the result of calibration carried out in advance under the same conditions using the standard sample of known permeability.

In the invented exothermic device, at least part of the exposed surface of at least either of the substrate and the covering material has formed thereon an adhesive layer at any time before inclusion in the gas-tight outer bag. In this case, the other gas-permeable side is preferable for it is then directly applicable to the body surface or fixable to be used with clothes.

As to this adhesive layer, there is no particular limitation as long as it is adherable to a skin surface, but specifically cited, for example, a layer comprising a wet compress agent or an adhesive.

As the aforementioned adhesive layer, layers may be prepared by the use of solvent-type adhesive, emulsion-type adhesive or hot-melt type adhesive.

As preferred adhesive layers, layers specifically containing, for example, rubbery adhesive agents, vinyl acetate adhesive agents, ethylene-vinyl acetate adhesive agents, polyvinyl alcohol adhesive agents, polyvinyl acetal adhesive agents, vinyl chloride adhesive agents, acrylic adhesive agents, polyamide adhesive agents, polyethylene adhesive agents, cellulose adhesive agents, polysulfide adhesive agents and hot-melt type high-polymer-containing adhesives but, of these, preferred are the layers containing rubbers adhesives, acrylic adhesives and hot-melt type high-polymer-containing adhesive agents proper for direct sticking to the skin, being less stimulative to the skin and less drop in adhesiveness even if a hot compress agent is added and particularly preferred is the adhesive layer containing the hot-melt-type high-polymer substance for its excelled initial tacking force and extremely good adhesiveness at the warming temperature.

There is no particular limitation for the thickness of such adhesive layers but normally in a range of 5 to 1000 μm, preferably 10 to 500 μm and more preferably 15 to 250 μm. If the thickness of the adhesive layer is less than 5 μm, the required adhesive force may possibly be difficult to obtain, while, if it is in excess of 1000 μm, bulky feel becomes disagreeable and less preferable also for cost reasons.

As hot-melt type high-polymer substances usable for the invented exothermic devices are specifically, for example, A-B-A type block copolymers, saturated polyester-type high-polymer substances, polyamide-type high-polymer substances, acrylic-type high-polymer substances, urethane-type high-polymer substances, polyolefin-type high-polymer substances and polyolefin-type copolymers, denatured substances thereof and mixtures of two or more thereof.

The aforementioned denatured substance is one having a part of ingredients of a hot melt-type high-polymer substance substituted by other ingredients for, for example, improvement of adhesiveness or modification of stability etc. of the hot melt-type high-polymer substance.

In the aforementioned A-B-A type block copolymers the "A" block represents monovinyl-substituted aromatic compounds such as styrene and methyl styrene, being thus a block non-elastic polymers, and "B" block represents a block of elastic polymers or conjugate dienes such as butadiene and isoprene, specifically, for example, styrene butadiene styrene block copolymer and styrene-isoprene-styrene block copolymer, and these may possibly be mixed properly.

As examples of commercially available products of the A-B-A type block copolymers are given, Cariflex TR-1101, Cariflex TR-1107, Cariflex TR-1107, Cariflex TR-1111 manufactured by Shell Inc.) and Solprene 418 manufactured by Phillips Petroleum Inc.

If desired, such adhesives may be admixed with proper amounts of other components such as other adhesives, adhesiveness-imparting agents, anti-aging agents, fillers, adhesion adjusters, adhesion improving agents, colorants, defoamers, tackifiers, modifiers, mildewproofing agents antibacterial agents, insecticides and/or deodorants.

Such adhesive layer may be formed on the exposed surface of either of the substrate or the covering material by direct application. In order to make sure that the adhesive layer is secured on the exposed surface, it is preferable to roughen the exposed surface of the substrate or the covering material or to form the substrate or the covering material out of paper, woven fabric, knitted fabric, nonwoven fabric or foamed film so that the exposed surface becomes rough.

In the invented exothermic device it is preferred if the exposed surface of the substrate and/or the covering material is covered with a wet compress layer or a medication layer containing therein or carried thereby skin-absorbable medicines for this enables wet compress effect and medication effect in addition to hot compress effect. With the aforementioned skin-absorbable medicines there are no particular limitations as long as long as the medicines used are skin-absorbable but the medicines may include, specifically, skin-stimulant, anodyne/antiphlogistic agent, central nerve active agent (soporific/sedative, psychoneurotic agent, etc.), diuretic, hypotensive, coronary vasodilator, expectorant, antihistaminic, anti-arrhythmic, cardiac, adrenocortical hormone drug, and local anesthetic. One type of these medicines, or two or more types thereof may be used.

The amount of medication used is not limited as long as a medical effect is expected, but may be determined from the point of view of pharmacological effect and economy, the content of skin absorbable medicines is properly determined in a range of 0.01 to 25 parts by weight, and preferably 0.5 to 15 parts by weight, in relation to 100 parts by weight of the adhesive.

With the invented exothermic device, it is desirable to have ceramic powder or molding thereof radiating far infrared rays placed in the exothermic composition and/or in the adhesive layer side of the exothermic device for accomplishing the effect of far infrared rays.

The ceramic material radiating far infrared rays may be used together with or in place of the exothermic composition. This ceramic material may be enclosed in the pouch along with the exothermic composition, or may be carried by a carrier as is the exothermic composition. Further, the ceramic material may be carried by the adhesive layer.

In this case, the heating effect promotes blood circulation. When used with the skin absorbable medication, the ceramic material increases the skin absorptivity of the medication to enhance the general or local therapeutic effect.

The exothermic device thus obtained not only supplies warmth to the human body in water to help people enjoy pleasant life indoors, but also is sufficiently effective therapeutically as a warm compress means, and now they are being used widely to help cure local stiffness, symptoms accompanying pain and chill, for example, stiffness in the shoulder, stiffness in muscles, lumbago, chill in hands and feet, neuralgia, rheumatism, bruises, sprains and other diseases and disorders.

In the exothermic device according to the present invention, the substrate and/or the covering material are formed of film or sheet foam, nonwoven or woven fabric or porous film or sheet on one side or on both sides of a non-air permeable or gas-permeable film or sheet, this being desirable for it ensures against movement or irregular displacement of the exothermic composition when a fluid exothermic composition is laminated on one side, and it is particularly desirable when the other side is covered with a nonwoven fabric or woven fabric for the feel or handling is markedly improved thereby.

In the invented exothermic device the invented composition formed as a fluid is used as laminating material and lamination is done by printing or coating, this allowing uniform and ultra-thin lamination, hence the exothermic device is ultra-thin and extremely soft and flexible, being very well adaptable to curved or bent parts of such as a shoulder and being also excelled in feel in use.

Since in the manufacture of the invented exothermic device the invented composition is used in a fluid form, the excessive moisture, free moisture or water-containing gel is used for barrier formation, this resulting in markedly slower progress of exothermic reaction involving the invented composition in the course of manufacture. While the loss of the invented composition due to exothermic reaction as a step of manufacture and deterioration of the quality of the exothermic composition or coagulation thereof is prevented, the water contained in the exothermic composition is absorbed into the pouch before use, the water content of the exothermic composition is suited for the exothermic reaction at the time of use, this resulting in marked improvement of the product such as the possibility of the exothermic temperature reaching the desired level at the time of use, and this, in turn, results in remarkably high quality and reliability of the product.

Moreover, in the invented exothermic device movement inside the pouch of the invented composition can be prevented, scattering of temperature or irregular displacement of the exothermic composition and partial gathering and resultant formation of high-temperature spots can also be prevented without fail, this ensuring against the risk of low-temperature burn, and the safety of this product is markedly raised.

Especially, since in the invented exothermic device the invented exothermic composition comes into direct contact at spots having water-absorbing property, the exothermic composition is attracted by the substrate and/or the covering material or the water-absorptive layer with absorption of excessive moisture in the invented composition or free moisture or water from the water-containing gel, this followed by a portion of the invented composition migrating into the substrate and/or the covering material or the water-absorbing member to give rise to the so-called anchoring effect which secures the invented exothermic composition in the substrate and/or the covering material or the water-absorptive member or the water-absorptive layer.

In this case, if the contact spots among the substrate and/or the covering material and the invented exothermic composition are formed of water-absorbable foam film or sheet, nonwoven or woven fabric or porous film or sheet, bondage with the invented composition is further improved and movement and irregular displacement of the invented exothermic composition is prevented more securely as well as various harms caused by irregular distribution of the invented exothermic composition.

Where in the invented exothermic device the substrate and/or the covering material or the water-absorptive layer is/are water absorbent, a part of the water in the invented exothermic composition is absorbed before use, this allowing adjustment of the water content of the invented exothermic composition to a level suited for exothermic reaction. If this is done, it is possible to have the exothermic reaction readily started with breaking of the gas-tight bag and the predetermined exothermic temperature is attained quickly and as the exothermic reaction proceeds, the water vaporized from the exothermic composition is replenished with water discharged from the substrate and/or the covering material, this allowing maintenance of the required exothermic temperature over a long period of time.

In the invented exothermic device, if either or both sides of the invented exothermic composition is/are covered with a thin film or sheet of water-absorptive material especially paper or high water-absorbency, a portion of the water retained in the invented exothermic composition is absorbed and the exothermic composition is securely fixed to the water absorptive material.

In the invented exothermic device, if the adhesive layer at least one of far infrared ray radiator, magnetizer or skin absorption medication is contained therein or carried thereby, far infrared ray heating effect, far infrared ray therapeutic effect, magnetic therapeutic effect and medication-induced therapeutic effect can naturally be expected but such effects may be further enhanced synergetically such general or local effect as the enhanced blood circulation by the warmth generated by exothermic reaction.

Next, the first method of the invention will be described in detail.

In the first method of the invention what is performed first is the step (A) for manufacture of an exothermic composition, i.e., the invented composition is formed as a fluid. The invented substance used here is the same as that described above.

For manufacturing the invented substance there are two alternative methods of throwing all of the aforementioned components in a mixer, this is followed by uniform mixing, or of throwing in all solid components of the aforementioned components, uniformly mixing these components in the mixer, then adding water and the resulting aqueous solution of metal halide or dispersion before mixing are useful for obtaining the aforementioned exothermic component. As to the mixer, there is no particular limitation as long as the components of the invented composition are uniformly mixable but also usable are, specifically, ribbon mixer, spallation mixer, screw blender, roll mixer, Banburry mixer and kneader.

Where in the manufacture of the invented composition water content is excessive, for example, when it is fluid, any kind of mixer may be used. Meanwhile, when the exothermic composition is fluid, the proportion of water is relatively small, hence the use of an apparatus such as a mixer or a kneader for kneading components under pressure is easy for making the exothermic composition fluid and, moreover, the squeezed-out water becomes free of moisture and after manufacture of the fluid exothermic composition the free moisture is absorbed by the gel in the periphery of the exothermic composition, hence this free moisture or water-containing gel as a barrier layer against contact with air, being thus effective for stabilization of the exothermic composition.

In the present invention the invented substance obtained in the step (A) is then transferred to and laminated in at least a given region in the upper surface of a thin substrate in the next step (B).

The substrate used here is the same as what was described in relation to the invented exothermic device, hence description thereof is omitted for avoiding repetition.

In the step (B) of the invented composition, the invented composition is transferred or laminated in a given shape on the upper surface of the substrate by printing or coating but the invented composition may possibly be laminated at one or two or more spots sidewise on the upper surface of the substrate or zigzag longitudinally.

In the present invention the invented composition is covered with a thin covering material in the step (C).

The covering material used here is the same as what was described in relation to the invented exothermic device, hence description thereof is omitted for avoiding repetition.

Here the substrate and the covering material are stuck together with the invented composition in between. Since the invented composition plays a role similar to that of an adhesive, it is not essential to have the composition and the covering material sealed along the periphery of the invented composition, but it is desirable to have this sealing along the periphery of the invented composition by sticking, heat-adhesion or thermofusion for further improvement of the product's quality as well as its reliability.

Since the first method of the present invention is for manufacturing the invented exothermic device which generates heat through contact with air, at least either or a part of the aforementioned substrate and the covering material is required to be gas-permeable.

In the method of the present invention a thin sheet of water-absorptive material may be applied to either or both sides of the invented composition to have a part of the water present in the invented composition absorbed thereby. Specific examples of this water-absorptive material are cited above.

In the first method of the present invention the invented composition is a fluid consistency, this giving rise to the various merits described below.

In the first method of the present invention lamination by printing such as screen printing or coating is extremely easy when an exothermic composition is fluid, i.e., the invented composition, is used, and ultra-thin exothermic devices are manufacturable at a high speed. Moreover, the method allows uniform distribution of the exothermic composition in the pouch and, further, when the invented composition is placed or sandwiched between the substrate and the covering material of foam film or sheet, papers, nonwoven or woven fabric or porous film or sheet, the invented composition with its high penetrating and anchoring effect gets into pores of such substrate and covering material and thus movement or irregular displacement thereof in the pouch is prevented.

In this case, especially when the composition and/or the covering material is/are water-absorptive and the invented composition is laminated on the substrate or a water-absorptive layer is first laminated and the invented composition is laminated thereon, this is followed by coverage with the aforementioned covering material, whole or a portion of the exothermic composition is fixed to the water-absorptive substrate and/or the covering material or water-absorptive layer formed thereon and its movement or irregular displacement is prevented more securely.

Lamination by printing or coating enables extreme thinning of this exothermic device and the resulting thin exothermic device with its per-hour progress of exothermic reaction is effective for excessive exothermic reaction of the exothermic composition and has such other features as being soft and flexible, being better adaptable to expansion and shrinkage of the outer cover and being improved in feel in use.

Further, in the first method of the present invention, if the adhesive aqueous solution of the water-absorptive agent is contained in or deposited on the sheet forming the pouch such as foam film or sheet, paper, nonwoven or woven fabric or porous film sheet by impregnation, spraying or kneading, or the thin pouch first made water-absorptive and then laminated with the invented composition by screen printing or coating, this followed by drying, the step of throwing-in dust can be eliminated and plant control well meeting GMP supposed to be applied in the near future to the manufacture of medical instruments and medicines. As a water-absorptive agent used here, the aforementioned water-absorptive polymer or tackifier may be cited.

Thus, the first method of the present invention has such various merits as mentioned above since the invented composition is a fluid but this invented composition is very well suited for transfer or lamination by printing or coating, this allowing high-speed manufacture of extremely thin exothermic devices, and is remarkably small in specific surface area compared with powdery exothermic compositions and the resultant decrease of air supply causes substantial stopping of the exothermic reaction to thereby enabling elimination of loss due to exothermic reaction in the course of manufacture and prevention of lowering of the quality of exothermic composition and coagulation thereof.

If, in the first method of the present invention, the excessive moisture, free moisture and a portion of the water. In the water-containing gel is absorbed by the pouch material such as the substrate and/or the covering material, loss of the water barrier and the resulting enhancement of contact with air of the now porous exothermic composition cause improvement of the temperature properly in use.

In the first method of the present invention, this exothermic composition can be laminated on the substrate by transfer or by printing, this enabling high-precision control of the laminating region and formation of extremely thin and uniform layer of exothermic composition film, the result being the possibility of high-speed manufacture of ultra-thin sheet of the invented exothermic composition.

In the first method of the present invention, the water content of the invented composition is raised to such an extent that its solution is fluid as it is laminated on the substrate. Since, however, water is absorbed by the substrate and/or the covering material or the water-absorptive layer, the exothermic reaction of the invented composition is scarcely noticeable at the time of manufacture, hence the loss due to exothermic reaction in the course of manufacture can be prevented as well as lowering of quality of the exothermic composition and coagulation thereof and, furthermore, a portion of the water content of the invented composition is absorbed by the substrate and/or the covering material or the water-absorptive layer so that the water content becomes proper for the exothermic reaction by the time of use, this resulting in increased reliability of the invented exothermic device.

In the first method of the present invention, the invented composition used is a fluid and can be accurately laminated in the predetermined region on the substrate without undue loss, this enabling manufacture of the invented exothermic device for effectively warming any specific region, hence an excellent warming effect and blood-circulation promoting effect are effectively obtainable. Another remarkable feature is that there is no risk of dust diffusion in the process of manufacture, hence plant control perfectly meeting the GMP standards applicable in the near future to the manufacture of medical appliances and medicines.

In the first method of the present invention, the process of laminating the fluid exothermic composition, covering the same with the covering material and packing the made exothermic devices is feasible integrally and in a very short period of time, hence there is no risk of the exothermic composition being subjected to conditions possibly triggering exothermic reaction and there is no likelihood of the invented composition generating heat in the course of manufacture.

As the result, lowering of the quality of the invented composition or coagulation thereof in the course of manufacture can be completely precluded, known harms such as lowering of yield, handling difficulty, complexity of machine maintenance, limitation of machine's operating hours and worker's working hours and the difficulty of disposal of coagulated compositions can be all eliminated and the high-quality and highly reliable exothermic devices can thus be obtainable at a still lower cost.

Then the second method of the present invention will be described in detail.

According to the second method of the present invention, the invented composition is first produced and after laminating the same in at least one predetermined region on the upper surface of the thin substrate at least one of iron powder, carbon component and water-absorptive agent is laminated or sprayed and the thin covering material is placed to cover the selected one of iron powder, carbon component and water-absorptive agent, featuring that either or a part of the aforementioned substrate and the covering material is gas-permeable.

According to the second method of the present invention, a film or sheet of water-absorptive material may be applied to either or both surfaces of the invented composition for a part of the water in the invented composition to be absorbed thereby. Specific examples of this water-absorptive material are cited above. In this case, either or both sides of the invented composition is/are meant side/s of the invented composition laminated by of sprayed with at least one selected from iron powder, carbon component or water-absorptive agent.

Hence, the covering material is placed to cover at least one selected from the invented composition, iron powder, carbon component and water-absorptive agent.

According to the second method of the present invention, the invented exothermic device is of the type generating heat through contact with air, hence at least part of the pouch formed of the aforementioned substrate and/or the covering material is gas-permeable. The substrate and the covering material are the same as those explained in relation to the invented device, hence explanation about these will be omitted for avoiding repetition.

The second method of the present invention is different from the first method of the present invention only in that at least one selected from iron powder, carbon component and water-absorptive agent is laminated or sprayed on the upper surface of the invented composition and then place a thin covering material to cover the selected one of iron powder, carbon component and water-absorptive agent, being the same as the first method of the present invention, hence explanation thereof will be omitted for avoiding repetition.

According to the second method of the present invention, the invented composition, i.e., the exothermic composition made fluid by increasing the water ratio to a level required therefor, is formed, this invented composition is laminated in at least one of the predetermined regions on the upper surface of the thin substrate, then the laminated upper surface is laminated or scattered with at least one selected from iron powder, carbon component and water-absorptive agent, this followed by placing a film or sheet of covering material to cover the same, and thereafter using the invented composition to cause the substrate and the covering material to be bonded together and, moreover, it is so arranged that a portion of the water present in the invented composition is absorbed by the substrate or the covering material or the water absorptive agent, featuring high-precision control or the region to be laminated, extremely small film thickness attainable, the possibility of laminating the surface of the substrate uniformly with the invented composition, the possibility of producing an extremely thin layer of the invented composition at a high rate and, further, the possibility of improving the initial rise of temperature or temperature property by inter-layer lamination or scattering of iron powder. Also, according to the second method of the present invention, the exothermic substance present in the invented composition is covered by the excessive moisture, free moisture or water-containing gel, the contact with oxygen of air is suppressed by the presence of excessive moisture to thereby prevent exothermic reaction of the exothermic substance, this resulting in preclusion of loss due to exothermic reaction and prevention of lowering of the quality of the invented composition and coagulation thereof in the course of manufacture. After completion of manufacture of the invented composition, the aforementioned water present in the invented composition is absorbed by the water-absorptive agent laminated or scattered, the substrate and also the covering material, this resulting in that the water content of the exothermic composition in the exothermic device will be optimum for an exothermic reaction by the time it reaches an end user.

Since, according to the second method of the present invention, the process of laminating a fluid exothermic substance on the substrate and of placing the covering material to cover the same and subsequent step of packing the completed exothermic devices can be made integral and the time required is extremely short, hence there is little chance for occurrence of conditions in the manufacturing process causing an exothermic composition to generate heat and heat generation of the invented composition in the manufacturing process is thus precludable.

As a result, lowering of the quality of the invented composition or coagulation thereof in the course of manufacture can be completely precluded, known harms such as lowering of yield, handling difficulty, complexity of machine maintenance, limitation of machine's operating hours and worker's working hours and the difficulty of disposal of coagulated substances can be all eliminated and the high-quality and highly reliable exothermic devices can thus be obtainable at a still lower cost.

Next, the third method of the present invention will be described in detail.

According to the third method of the present invention, first the invented exothermic composition is laminated on a thin substrate, then a film or sheet of covering material is placed to cover the same and the aforementioned substrate and covering material are stuck together by the viscosity of the invented composition for completion of a laminate.

In this case, a sheet or film of water-absorptive layer may possibly be applied to either or both sides of the invented composition.

According to the third method of the present invention, the invented composition used is the same as described above, hence explanation about it will be omitted for avoiding repetition.

According to the third method of the present invention, too, since the oxidation reaction, i.e., exothermic reaction is suppressed even if the invented composition comes into contact with air until a part of the water present in the invented composition is absorbed by the water-absorptive substrate and/or the covering material. Hence loss of the exothermic composition due to the exothermic reaction during manufacture, lowering of the quality of the exothermic composition and coagulation thereof can be almost surely prevented. Moreover, the invented composition is a fluid, this permits lamination in a uniform thickness. Further, the invented composition is viscous, being also adhesive to the pouch, hence movement or irregular displacement of the exothermic composition can be prevented and excessive exothermic reaction of the exothermic composition is precludable.

According to the third method of the present invention, there is no particular limitation with regard to the method for laminating the invented composition on the substrate but specifically cited are, among others, coating by the use of a coater such as head coater, roller, applicator and the like.

Since the third method of the present invention is for obtaining the invented exothermic device generating heat through contact with air, either the aforementioned substrate or the covering material or at least a part thereof is gas-permeable. Since the substrate and the covering material are the same as those described in relation to the invented exothermic device already described, hence explanation about these will be omitted for avoiding repetition.

According to the third method of the present invention, the exothermic device is obtainable by stamping out the resulting laminate in a predetermined shape. Hence, the substrate and the covering material are required to be easy to stamp out and from this viewpoint it is desirable to use paper or the like as material of the substrate and the covering material.

The aforementioned step of stamping-out pieces of predetermined shape from the aforementioned laminate may also be done with the laminate kept stationary and, should it be the case, a large number of exothermic devices can be made at once by doing stamping-out simultaneously with a plurality of laminates fixed along the feeding direction and also along the sidewise direction at proper intervals, this being effective also for cost reason.

This method is, however, problematic as follows. When, as mentioned above, the invented composition is laminated on a thin substrate being played out of a roll film or roll sheet at a speed of 160 to 200 m/min, and then a thin covering material being played out of another roll film or roll sheet is placed thereon for continuous formation of a laminate, stopping the laminate in the stamping-out process means the necessity of winding back the formed laminate once and then playing out intermittently. This complicates the manufacturing process with prolongation of the required time and, worse, intermittent stamping-out operation interferes with the desired improvement of the working efficiency.

According to the third method of the present invention, it is preferable to obtain the invented exothermic devices using a roll press for stamping-out in any arbitrary shape with the laminate being fed at the feeding speed in the manufacturing process therefor, for example, 160 to 200 m/min.

When a roll press is used, continuous stamping-out of laminate is feasible and, moreover, manufacture of the laminate and stamping-out can be integrated to enable continuous operation, hence a large number of exothermic devices can be manufactured with the cost much less than in the method of stamping-out the laminate intermittently.

The above method is further improved in working efficiency as well as in cost reduction when stamping is done at two or more spots sideways with the substrate or the like being fed continuously and especially when longitudinal stamping-out is done in a zigzag fashion, this resulting in a much more saving of the cost.

The stamping-out shape may arbitrary according to the intended use for the obtained exothermic device.

According to the third method of the present invention, the obtained laminate is stamped in any desired shape but the stamped-out pieces of the invented exothermic device are not particularly limited for use such as for a foot, shoulder and waist.

According to the third method of the present invention, the substrate and the covering material are stuck together by the viscosity of the invented composition but thereafter a part of the water is absorbed by the substrate and the covering material and the exothermic devices thus obtained are commercially valid for they are distributed after sealing in non-gas-permeable outer bags.

However, it is desirable to interpose the stamped-out piece of the invented device between two other layers of film or sheet, to have the two layers of film or sheet stamped into a size greater than the stamped-out piece of the invented exothermic device at the time of or after the insertion thereof and then to seal together the two layers of film or sheet along the periphery of the aforementioned invented exothermic device at the time of or after the stamping-out operation.

Here, at least either or a part of the aforementioned two layers of film or sheet is gas-permeable and thus the obtained invented exothermic device is further improved in reliability.

That is, an invented exothermic device of an arbitrary shape is obtained in this process but the volume of air supplied to the exothermic composition inside thereof is controlled by the gas-permeability of these two layers of film. Hence the gas-permeability or suppliability to the invented composition is controlled on the basis of moisture-permeability like that of the substrate and/or the covering material. The humidity-permeability of either of the two layers of film or sheet or of laminate of film/sheet as substrate and covering material is the same as in the case of the invented composition and the invented exothermic device, hence explanation about it will be omitted for avoiding repetition.

The aforementioned two layers of film or sheet are either gas-permeable or non-gas-permeable and these may possibly be adhesive, hot-melt bondable or heat-sealable.

The aforementioned adhesive film or sheet includes a base film or sheet and a gas-permeable adhesive layer formed thereon. Such an adhesive layer is made entirely of a gas-permeable hot-melt adhesive or is made of part of a gas-permeable adhesive and part of a non-gas-permeable adhesive. The base film or the base sheet itself may not be necessarily heat-melt bondable or heat-sealable.

According to the third method of the present invention, if the lengthy exothermic composition is already made, two layers of film or sheet may be sealed together along the periphery of the individual exothermic devices before, during or after stamping.

Stamping-out pieces of film or sheet are required to be greater in size than that of the particular exothermic device and also required to be similar or substantially similar in shape thereto and it is desirable if the size of the former is greater by several mm to 20 mm along the entire periphery (extended edge).

According to the third method of the present invention, the aforementioned tow layers of film or sheet are to be sealed together in the extended edge or along the entire periphery of the exothermic device by sticking, heat-adhesion, or thermofusion.

According to the first to the third method of the present invention, either side of the invented exothermic device is desired to have the whole of a part of the exposed area covered with an adhesive layer and at least part of the opposite side is desired to be gas-permeable.

The adhesive layer may possibly be a wet compress layer containing a wet compress agent or a medication layer containing or carrying skin absorbable drugs, but since this is the same as in the case of the invented exothermic device, explanation about it will be omitted for avoiding repetition.

The adhesive layer may have contained therein or carried thereby at least one of far infrared ray radiators or magnetic means.

According to the first to the third method of the present invention, a part of the water present in the invented composition is absorbed by the substrate and/or the covering material or by the water-absorptive material applied to either or both sides of the invented composition from the time of its manufacture by the time it is actually used, and the free moisture or a part of the water present in the water-containing gel is absorbed by the substrate and/or the covering material or the water-absorptive material applied to either or both sides of the invented composition. This results in a formation of a porous exothermic composition which makes good contact with air and readily causes an exothermic reaction upon contact with air.

According to the third method of the present invention, the invented composition, namely a fluid exothermic composition, is laminated on the film substrate and the thin covering material is placed to have it enclosed thereby, the aforementioned substrate and the covering material are stuck together by the viscosity of the invented composition, then the resulting laminate is stamped for formation of pieces of any desired form and at least either or part of the aforementioned substrate or the covering material is gas-permeable.

Hence, an extremely thin exothermic device is manufacturable and, moreover, the invented composition, i.e. a fluid exothermic composition, is used, hence the exothermic reaction is controllable through barrier formation by excessive moisture or the like, this possibly causing elimination of loss due to exothermic reaction in the course of manufacture, and preclusion of various harms caused by prevention of lowering of the quality of the invented composition and coagulation thereof and, furthermore, uniform distribution of the invented composition in a pouch or causing it to be fixed thereto enables preclusion of movement or irregular distribution of the exothermic composition, this enabling preclusion of excessive exothermic reaction of the exothermic composition for prevention of low-temperature burn and, further, allowing manufacture of the invented exothermic device quite safe to use.

According to the first to the third method of the present invention, application of a thin sheet of water-absorptive material, especially highly water-absorbable paper to either or both surfaces of the invented composition, a part of the water present in the invented composition can be absorbed by the paper and, furthermore, secure fixing of such paper to the invented composition is caused thereby.

DETAILED DESCRIPTION OF THE PREFERRED EMBODIMENTS

Embodiments of the present invention will particularly be described hereinafter with reference to the drawings. It should be understood, however, that the present invention is not limited to these embodiments.

Figure 1:
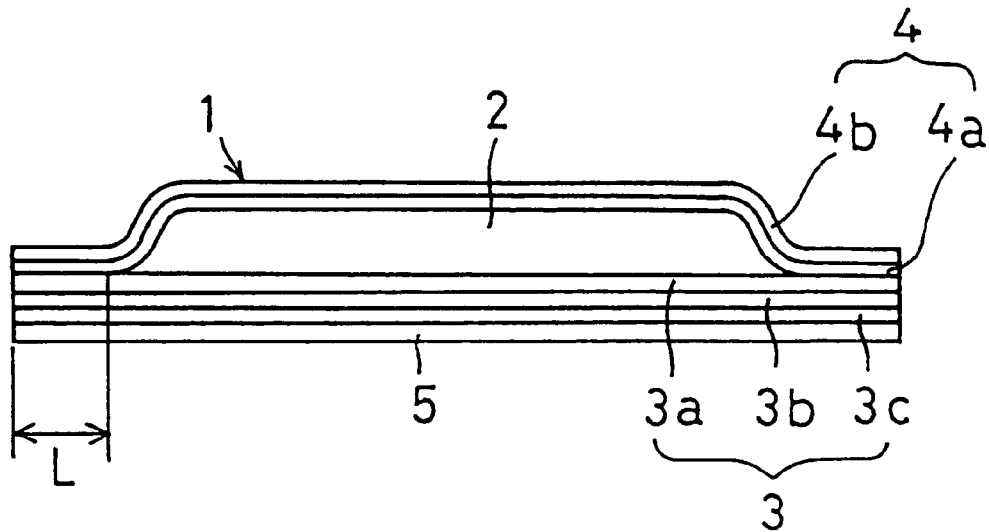
FIG. 1 is a schematic sectional view of an exothermic device in a first embodiment of the present invention.

An invented exothermic device referred to in a first embodiment of the present invention has, as shown in the schematic sectional view of FIG. 1, a fluid exothermic composition, i.e., the invented composition 2, sealed in a flat and rectangular pouch 130 mm long and 95 mm wide, the aforementioned pouch 1 is, in this case, made of a non-gas-permeable substrate 3 and a gas-permeable covering material 4 and, moreover, an adhesive layer 5 to 100 μm thick is formed on the exposed surface of the substrate 3.

The substrate 3 is made of a non-gas-permeable polyethylene film 3b40 μm thick for being sufficiently soft and flexible and having formed on one surface thereof a water-absorptive polymer-containing polyester nonwoven fabric (Sanwet IM-5000MPS 10 g/m$^2$ and 210 μm thick) 3a and on the other surface a nonwoven fabric made of rayon/polyester blend containing 60% by weight of rayon (140 μm thick) 3c.

The covering material 4, which is required to be high in mechanical strength and also required to be sufficiently soft and flexible, may, for example, be made of porous polyethylene film 4a having a thickness of about 100 μm laminated on one side with nylon nonwoven fabric 4b150 μm thick.

This covering material 4 has its humidity-permeability (humid permeable volume as measured by the Lyssy method) adjusted to be 400 g/m$^2$ 24 hr.

Further, the adhesive layer 5 is for adhesion of the pouch to the outer bag, and this adhesive layer 5 is formed of an adhesive of styrene-isoprene-styrene block copolymer type.

The manufacturing method for the invented composition 2 is as follows.

Per 70 parts by weight of iron powder as an effective component (KP manufactured by Dowa Teppun K. K.) active carbon as carbon component (GL-50 manufactured by Noritto K. K.) in 10 parts by weight, common salt (sodium chloride) as a metal chloride in 2 parts by weight, tackifier (Metrose 60SH-4000 manufactured by Shin'etsu Kagaku K. K.) in 0.7 parts by weight, surface active agent (Metrose 60SH-4000 manufactured by Kao K. K.) in 0.2 parts by weight and sodium tripolyphosphate as pH adjuster in 0.1 part by weight are mixed and the resulting mixture is admixed with water for its viscosity adjusted to be approximately 250,000 cps at 20° C.

That is, active carbon, tackifier, surface active agent, pH adjuster, common salt and iron powder were added in this order and, moreover, in the aforementioned mixing ratio, in a mixer (T. K. Hubismix 2P-100 type and 100 liters by volume manufactured by Tokushu Kika Kogyo K. K.) and after mixing for 5 minutes water was added in portions under stirring and thereafter kneading was continued for 15 minutes.

Thereafter, the blade and the vessel were cleaned and followed by measurement of viscosity and specific gravity. The water ratio was adjusted in the following way until the viscosity of the mixture came to be approximately 250,000 cps. The water ratio was 40 parts by weight per 100 parts by weight of iron powder (DKP manufactured by Dowa Teppun K. K.). The viscosity of the resulting invented composition was 230,000 cps.

The rate of revolution of the blade was kept at 10 rpm from the start to the end of the test.

When his invented composition was kept at 10° C. for one hour, some increase in viscosity was noted and the viscosity measured by the following method after repeated kneading was 250,000 cps, and this was laminated on the substrate 3 by screen printing.

In this case, too, the rate of revolution velocity of the blade was kept at 10 rpm from the start to the end.

The aforementioned viscosity is the result of measurement taken by the use of a Viscometer BH-type manufactured by Tokimec Inc, and the rotor #7 with its revolving rate kept at 2 rpm, and the beaker's inside diameter was 85φ mm as directed and the measuring temperature was 20° C.

The invented composition 2 being a fluid is small in specific surface area, this meaning less chance for contact with air and, furthermore, the possibility of contact with air of the iron powder is reduced by the presence of free moisture and water-containing gel. The per-hour oxidation volume is aggravated by lamination by the film or sheet covering material and the oxidative reaction is almost retarded before manufacture of the exothermic device is completed.

Thus, the invented substrate is a fluid, this allowing lamination thereof on the upper surface of the water absorptive polymer-containing polyester nonwoven fabric 3a by screen printing and resulting in the possibility of high-precision control of the laminated region. Moreover, it is now possible to control the layer thickness to be extremely small and even uniform and it is even possible to prevent movement inside the pouch 1 through bondage of the nonwoven fabric 3a of the water-absorptive polymer-containing polyester blend to the invented composition 2. Further, reduction of the layer thickness of the invented composition 2 enables extreme thinning of the exothermic device.

In this embodiment the filmy substrate 130 mm wide is played out of a roll film at a horizontal speed of 180 m per minute, the upper surface being meanwhile screen printed with the invented composition 2 to a layer thickness of approximately 0.5 mm. Immediately thereafter the printed layer is covered with the covering material 4, this followed by heat-sealing the space outside the printed region and subsequent and successive shearing along the sidewise center of the heat-sealed region and extremely thin exothermic devices each thereof having a sealed margin of L=7 mm along its periphery.

The individual sheared invented exothermic devices are then successively fed to the packing step for being sealed in gas-tight outer bags in an undisclosed way.

The invented composition 2 is printed on the upper surface of the substrate by a screen print. A part of the water contained is gradually absorbed therefrom and meanwhile the printed surface is covered by the covering material 4. The time required for enclosure in the outer bag by sealing is extremely short after printing which is extremely short and there is scarcely any likelihood of moisture being absorptive by the substrate to a degree for enabling the exothermic reaction.

There is scarcely any likelihood, either, of the invented composition 2 starting generating heat in the manufacturing process, and there is no risk of occurrence of loss due to exothermic reaction or lowering of the quality of the exothermic composition. There is practically no risk of the invented composition being coagulated to cause dropping of the yield, and various known harms such as interruption of operation, limitation about working hours, difficulty and risk accompanying cleaning of the machine or equipment, trouble of required frequent cleaning of the same or difficulty of treating or disposal of coagulated matters can be prevented.

When after the lapse of 24 hours the outer bag was broken and the uncovered normal exothermic device was stuck to the human skin, the exothermic temperature rose to approximately 38° C. in 1 to 2 minutes and thereafter the effect of heat generation was found controlling the temperature in a range of 38° C. to 41° C. for more than 9 hours. While in use no movement of the invented composition 2 was noticed inside the pouch 1 and uniform generation of heat was noticed all over.

Figure 2:
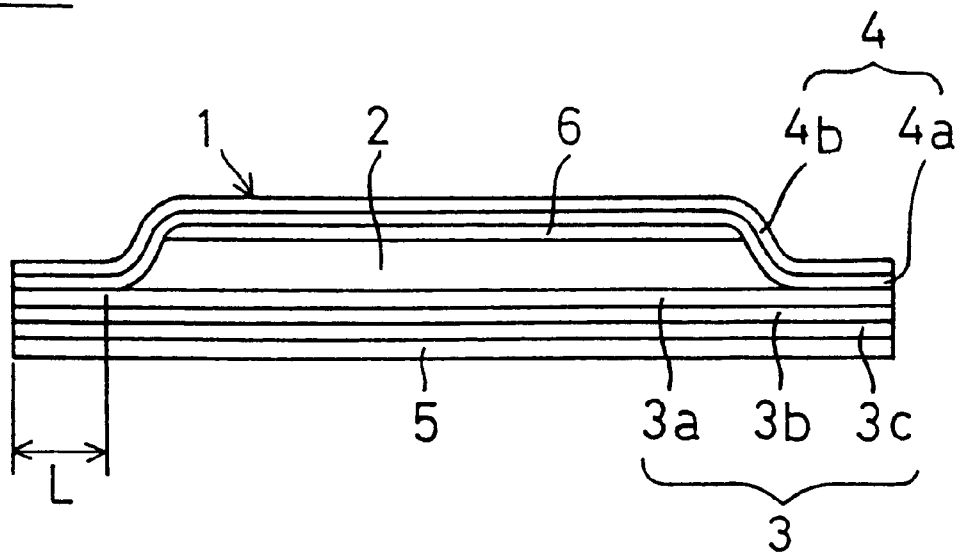
FIG. 2 is a schematic sectional view of an exothermic device in a second embodiment of the present invention.

The invented exothermic device according to the second embodiment of the present invention, as shown in FIG. 2 in the schematic sectional view, has the invented composition 2 sealed in a rectangular flat pouch 130 mm long and 95 mm wide, the bag 1 is formed of the non-gas-permeable substrate 3, the gas-permeable covering material 4 and in this case the exposed surface of aforementioned substrate 3 is covered with an adhesive layer 5 of styrene-isoprene-styrene block copolymer 100 μm thick.

The substrate 3, which is required to be sufficiently soft and flexible, is made of a core layer of polyethylene film of 40 μm thickness covered on both sides of nonwoven fabric 3a 3c of rayon polyester blend of 140 μm thickness having a rayon fiber content of 60% by weight.

The invented composition 2 and the adhesive layer 5 used in this embodiment were the same as those used in the first embodiment.

The invented composition 2 was laminated on the upper surface of the substrate 3 by screen printing and, thereafter, the water absorptive layer 6 (20 g/m² in METSUKE) was formed manually by scattering the water-absorptive agent (highly water absorptive resin Aquaclic CS-6HS manufactured by Nippon Shokubai K. K.) and then after covering the same with the covering material 4 the peripheral margin was heat-sealed, and the invented exothermic device having a heat-sealed margin L=7 mm wide was thus obtained.

In short, this second embodiment is essentially the same as the first embodiment described above in the manufacturing method and other constitutional features, hence explanation about them will be omitted for avoiding repetition.

Figure 3:
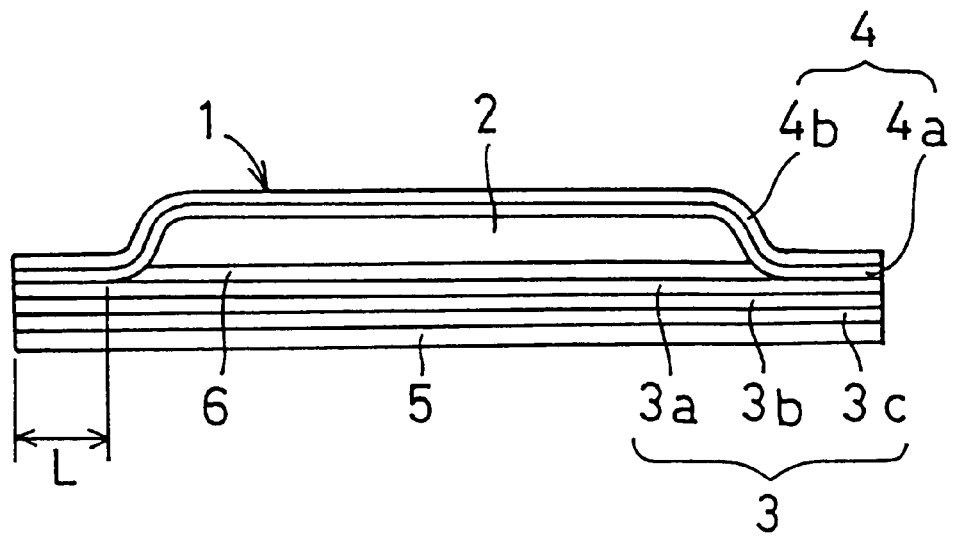
FIG. 3 is a schematic sectional view of an exothermic device in a third embodiment of the present invention.

The exothermic device referred to in this third embodiment is, as shown in the schematic sectional view of FIG. 3, essentially the same as described above except that the vertical relationship between the water absorptive layer 6 and the invented composition 2 is reversed.

That is, in this exothermic device, the water absorptive layer is 6 of 20 g/m² in specific basis weight was formed on the substrate 3 in the following way.

That is, the water absorptive agent (highly water absorptive resin Aquaclic CS-6HS manufactured by Nippon Shokubai K. K.) was used. Its 4% by weight aqueous solution was screen printed to a layer thickness of 500 μm and was dried, thereby obtaining the water absorptive layer 6 of 20 g/m² in a specific basis weight.

The invented exothermic device referred to in the third embodiment was made in the same way as described above except that the invented composition 2 was formed on the surface of the water absorptive layer 6 on the substrate 3.

After all, the manufacturing method and other constitutional features used was the same as embodiment 1 described above, its action and effect, too, being the same, hence explanation about them will be omitted for avoidance of repetition.

Figure 4:
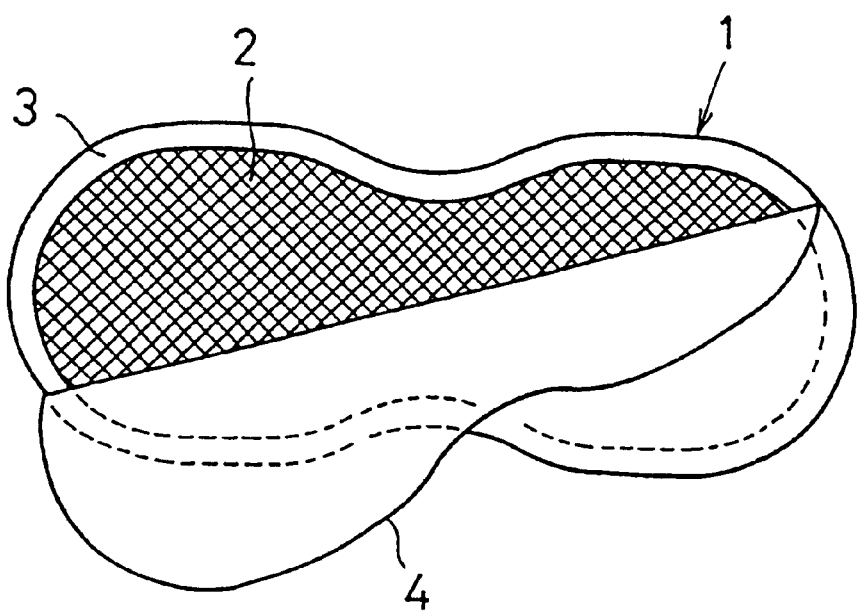
FIG. 4 is a schematic view of an exothermic device in a forth embodiment of the present invention.

The fourth embodiment of the present invention relates to an example made specifically adaptable to the shoulder made by the same method. The perspective view of this exothermic device specifically for the shoulder is shown in FIG. 4.

The water absorptive substrate 3 is first screen printed with the invented composition 2 in planar gourd shape as it is played out, then the exposed peripheral margin is coated with an adhesive and, thereafter, the covering material 4 is guided by a roller to be laminated thereon. Thus, the substrate 3 and the covering materials 4 is sealed with the invented composition 2 enclosed therebetween, this followed by formation of the adhesive layer 5 of 50 μm thickness on the exposed surface 1 of the substrate 3, the lengthy exothermic device thus obtained is extended by roll press to a size some 7 mm larger than the invented composition 2 with its form adaptable to the desired part of the shoulder, in the planar gourd shape in this embodiment.

The substrate 3 and the covering material 2 are then stuck together also by the enclosed invented composition 2.

Figure 5:
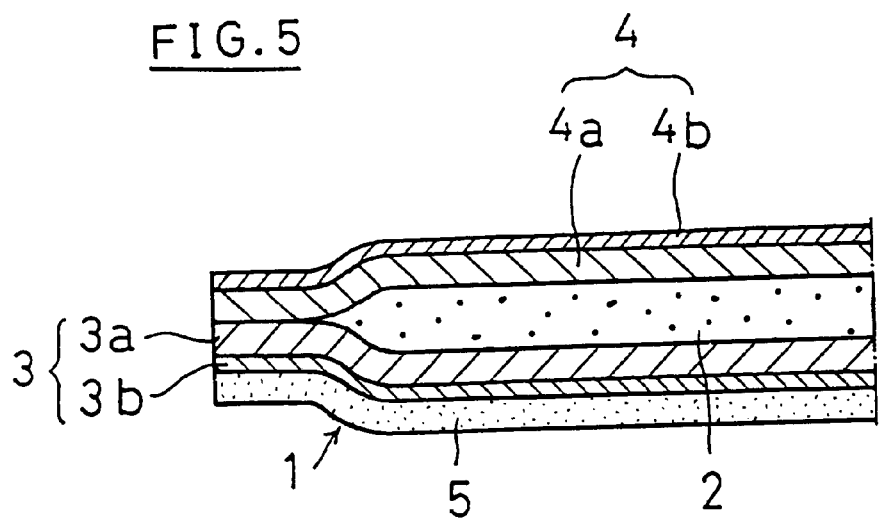
FIG. 5 is a sectional view showing essential parts of the exothermic device of the fourth embodiment of the present invention.

As shown in the sectional view of FIG. 5, water absorptive rayon nonwoven fabric 3a approximately 80 g/m² in METSUKE is laminated with non-gas-permeable polyethylene sheet 3b approximately 50 μm thick and for that the substrate 3 is so printed as to allow direct contact of the invented composition 2 with one side of the rayon nonwoven fabric 3a.

The aforementioned covering material 4 is of water absorptive rayon nonwoven fabric 4a approximately 80 g/m² in MITSUKE laminated with a gas-permeable polyethylene 4b approximately 50 μm thick, its gas-permeability being 300 g/m²·24 hr. This covering material 4 has the invented composition 2 laminated on the rayon nonwoven fabric 4a so as to allow direct contact with the rayon nonwoven fabric 4a.

The aforementioned adhesive layer 5 is formed of styrene-isoprene-styrene block copolymer. For improved adhesion hereof to the substrate 3, the exposed region of polyethylene sheet 3b of the substrate 3 is roughened in advance by corona treatment with its wetting index to be in excess of 40 dynes.

The invented composition 2 was prepared as follows: Mixed into 100 parts by weight of iron powder as an exothermic substance (DKP manufactured by Dowa Teppun K.K.) were 0.21 parts by weight of water absorptive polymer (Sanwet IM-5000MPS manufactured by Sanyo Kasei K.K.) 1.4 parts by weight of tackifier (Celogen EP manufactured by Daiichi Kogyo Seiyaku K.K.), 4.21 parts by weight of active carbon (SA-SUPER manufactured by Noritto K.KL.) 4.87 parts by weight of sodium chloride as a metal halide and 0.25 parts by weight of sodium tripolyphosphate as a pH adjuster. The mixture was admixed with water so as to have its viscosity adjusted to approximately 3,000,000 cps. at 20° C.

That is, the active carbon, the tackifier, the water absorptive polymer, the pH adjuster, the sodium chloride and the iron powder in the given quantitative proportions thrown in this order into a mixer (T. K. Hybismix 2P-100 type, 100 litres by volume) and after stirring for 5 minutes, a proper amount of water was added, this followed by kneading for 15 minutes.

Thereafter the blade and the casing were cleaned and after resumed kneading for 20 minutes viscosity measurement and measurement of specific gravity were made. The water ratio adjustment was done in the following way so that the liquid's viscosity was adjusted to approximately 3,000,000 cps. The water ration determined in this case was 29.79 in parts by weight per 100 in parts by weight of the iron powder (DKP of Dowa Teppun K. K.) and the viscosity of the invented composition was 3,030,000 cps.

The blade's revolutional rate was kept at 10 rpm from start to end.

When the invented composition was kept for 1 hour at 10° C., some rise in viscosity was noted but after resumed kneading the viscosity measured in the following way was 3,050,000 cps and this was laminated on the substrate 3 by screen printing.

In this case, too, the blade's revolutional rate was kept at 10 rpm from start to end.

The viscosity was measured by the use of R110 type viscosimeter, RE 110U system, Detection Head RE100U and Controller RC100A manufactured by Toki Sangyo K. K. and the rotor used was of SPP type with its revolutional rate kept at 0.2 rpm. (D=0.4 (1/S) ) and measurement was taken at 20° C.

Hence, in this invented composition 2, free moisture or moisture present in the water-containing gel functions as a barrier, thereby retarding exothermic reaction almost totally.

When the invented composition 2 is screen printed on the substrate 3 to a layer thickness of 820 μm, the free moisture in the invented composition and moisture present in the water-containing gel are gradually absorbed by the water absorptive rayon non-woven fabric 3a and, further, after placing of the covering material 4 they are also absorbed by the rayon nonwoven fabric 4a and in time the amount of water within the exothermic composition 2 becomes optimum for creating the predetermined exothermic temperature.

While it takes rather a long time for the free moisture and moisture present in the water-containing gel to be absorbed by the substrate 3 and the covering material 4 so that the water ratio becomes optimum, the time required for the manufactured invented exothermic device to be enclosed or sealed in a non-gas-permeable pouch is extremely short, and there is no possibility of the water ratio of the invented composition 2 coming to be optimum for a rise of the exothermic temperature to the predetermined level.

Thus, there is no possibility of the invented composition 2 to generate heat before enclosing the exothermic composition in a non-gas-permeable pouch and there is no risk of the various known harms caused by coagulation of the product of exothermic reaction such as lowering of the yield, handling difficulty, complicated machine maintenance, limitations about the machine's operating hours and worker's working hours and difficulty of treating of or disposal of the coagulants.

Since the excessive moisture present in the invented composition 2 is absorbed by the water absorptive rayon nonwoven fabric 3a of the substrate 3 and the water absorptive rayon nonwoven fabric 4a of the covering material 4 so that the mix ratio of water will have come down to the optimum level for the predetermined exothermic temperature (reaction) by the time it reaches an end user, there is no possibility of deterioration of the invented composition 2 before the outer bag is torn and the invented exothermic device is taken out for contact with air. Thus, the quality of the invented composition 2 is retainable at a high level and when the bag is torn and the exothermic device is taken out, the exothermic reaction is initiated immediately for quick rise of the temperature to the predetermined level.

Moreover, the invented composition 2 has high fluidity and therefore can be laminated on the substrate 3 by such techniques as printing or coating; hence, when compared with the conventional powdery exothermic compositions which have no fluidity at all and are simply dropped onto the substrate 3, it is uniformly laminated in the predetermined region at a higher rate of speed with great accuracy.

When the aforementioned invented exothermic device was enclosed in a non-gas-permeable bag, and after lapse of 10 days, it was taken out of the bag torn open and then stuck to the skin of the shoulder, excellent warming effect was retained for more than 5 hours.

With regard to applicability of the invented exothermic device, the extreme thinness of the exothermic device makes it as a whole soft and flexible and mild in feel to the skin of the shoulder, it was readily deformable according to curvature of the shoulder, also well following the movement of any part of the shoulder, excelled in adherence where it is used, hence is no risk of peeling off during use, excelled in warming effect and effective for warming, among others, the shoulder.

While in use, the exothermic composition 2 does not move noticeably, the distribution of the exothermic temperature is uniform, there is no risk of low-temperature burn and improved safety is in use.

Then, the invented exothermic device for the back as embodiment 5 was manufactured in the same way as the fourth embodiment in a way unillustrated but similar to the fourth embodiment.

The invented composition 2 was prepared as follows: To 100 parts by weight of iron powder as an exothermic composition (GFP manufactured by Dowa Teppun K. K.), the following ingredients were added: 7.0 parts by weight of an active carbon (SA-SUPER manufactured by Noritto K.K.), 2.0 parts by weight of a diatomaceous earth (oblite) as a water retainer, 1.4 parts by weight of a tackifier (Celogen EP manufactured by Daiichi Kogyo Seiyaku), 0.3 parts by weight of a water-absorptive polymer (Sanwet IM-5000MPS manufactured by Sanyo Kasei K.K.), 5.0 parts by weight of a sodium chloride as a metal halide, and 0.3 parts by weight of a sodium tripolyphosphate as pH adjuster. The mixture was then added with water so that the viscosity became 2,500,000 cps at 20° C.

Specifically, the active carbon, the diatomaceous earth, the tackifier, the water adsorptive polymer, the pH adjuster and the sodium chloride were put in a mixer (T. K. Hybismix 2P-100 type, 100 litres by volume) in this order and in the above proportions. Then, the lid was closed so as to secure the mixer air-tightness. Then, while the mixture was stirred at 10 rpm, measurements on viscosity and specific gravity were conducted., the iron power was put into the mixer and stirred for 3 minutes. Water was then added while the mixture was still being stirred. then, the rate of revolution was raised to 15 rpm and the mixture was further mixed for about 5 minutes. The mixing was then stopped.

Thereafter, the blade and the casing were cleaned and after resumed mixing for 5 minutes at 1 rpm measurements on viscosity and specific gravity were conducted. The water ratio (proportion) adjustment was done in the following way so that the viscosity became around 2,500,000 cps. The water ratio determined in this case was 42.0 in parts by weight per 100 parts by weight of iron powder (DKP manufactured by Dowa Teppun K.K.). The specific gravity of the invented composition was 2.428 g/ml and the viscosity was 2,520,000 cps.

When the invented substance was kept for 1 hour at 10° C., some rise in viscosity was noted but after resumed kneading the viscosity measured in the following way was 2,550,000 cps, and this was laminated on the substrate 3 by screen printing.

In this case, too, the blade's revolutional velocity was kept at 10 rpm from start to end.

The viscosity was measured by the use of R110 type viscosimeter, RE 110U system, Detection Head RE100U and Controller RC100A manufactured by Toki Sangyo K. K.

and the rotor used was of SPP type with its revolutional velocity kept at 0.2 rpm (D=0.4 (1/S) ) and measurement was taken at 20° C.

Hence, in this invented composition 2, free moisture or water present in the gel serves as a barrier, thereby retarding the exothermic reaction almost totally.

When the aforementioned invented exothermic device was enclosed in a non-gas-permeable bag, and after lapse of 10 days, the invented exothermic device was taken out and then stuck directly to the skin of the back by using the adhesive layer 5. Excellent warming effect was noted for more than 6 hours.

With regard to applicability of the invented exothermic device, the extreme thinness of the exothermic device makes it as a whole soft and flexible and mild in feel to the skin, readily deformable according to curvature of the shoulder also well following its movement, excelled in adhesion to where it is used, there is no risk of peeling off during use, excelled in warming effect and effective for warming, among others, the back of the body.

While in use, the exothermic composition 2 does not move noticeably, the distribution of the exothermic temperature is uniform, hence there is no risk of low-temperature burn and improved safety is in use.

Another exothermic warming experiment was then made in the following way.

Iron powder (DKP manufactured by Dowa Teppun K. K.) in 70 parts by weight, active carbon as carbo component (GL-50 manufactured by Noritto K.K.) in 10 parts by weight, sodium chloride as a metal chloride in 2 parts by weight, tackifier (Metrose 60SH4000 manufactured by Shin'etsu Kagaku K.K.) in 0.7 parts by weight, surface active agent (Demol EP manufactured by Kao K. K.) in 0.2 parts by weight and pH adjuster (sodium tripolyphosphate) in 0.1 part by weight were mixed with addition of an excessive amount of water. Two kinds of fluids were prepared whose viscosities were 10,000 cps and 6,800,000 cps in viscosity respectively at 20° C.

An experiment was made using two specimens of the invented compositions 10,000 cps and 6,800,000 cps respectively.

Figure 6:
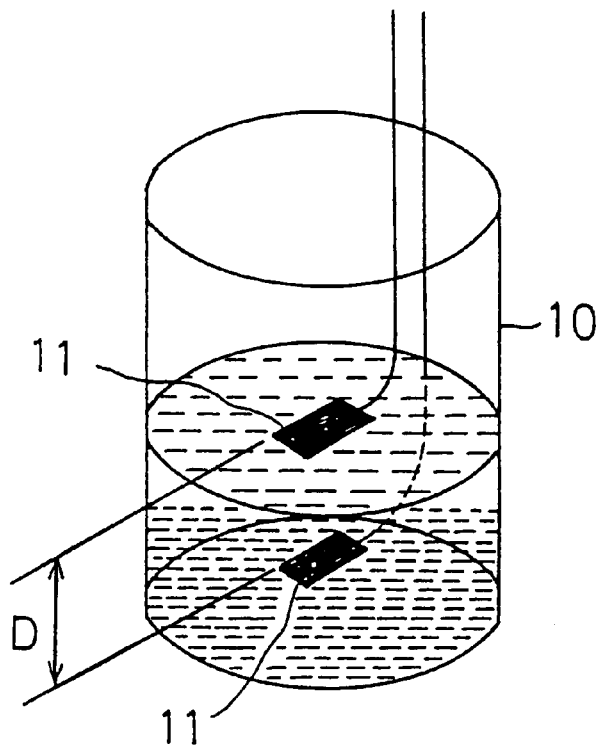
FIG. 6 is an explanatory view showing the test method used for investigating the stability of the exothermic composition.

The invented composition was put in a 200l beaker 10, and, as shown in FIG. 6, two temperature sensors were configured in such a way that one of them was placed at the surface and the other one was at the location 10 mm below the center of the surface (position D) so as to measure the temperature difference.

The result showed that, with the specimen 10,000 cps in viscosity there was scarcely noted any rise in temperature within approximately 20 minutes either in the surface or beneath the center of the surface, with the other specimen 6,800,000 cps in viscosity rise in temperature was noted in the surface after approximately 5 minutes, but rise in temperature was scarcely noticeable then beneath the center of the surface.

Meanwhile, a comparative experiment was made using an exothermic composition comprising iron powder 60 in parts by weight, 10% by weight of table salt solution in 25 parts by weight, active carbon in 13 parts by weight and wood flour 14 in parts by weight, the iron powder, table salt and the active carbon being the same as used in the aforementioned embodiment.

With this composition, however, a viscosity measurement was performed.

In the comparative experiment made using this specimen, rise in temperature was noted almost instantly in the surface as well as beneath the center of the surface and in some cases the temperature was seen exceeding 60° C. after some 2 minutes.

In the present invention, the above described embodiments may be combined properly but also preferred is application of a film or thin sheet of water absorptive materials such as highly water absorptive paper to either or both sides of the invented composition, this being effective in two ways, i.e., absorption of a part of water or vapor by such paper and a more secure adhesion of the invented composition thereto.

The foregoing relates to preferred exemplary embodiments of the invention, it being understood that other variants and embodiments thereof are possible within the spirit and scope of the invention, the latter being defined by the appended claims.

What is claimed is:

1. An exothermic device comprising a thin flat pouch having opposed inner surfaces, a thin substrate and a thin covering material, at least a portion of said thin pouch is gas-permeable and water absorbable, said thin pouch being provided with a non-odor producing fluid exothermic composition laminated and sealed therewithin, said fluid exothermic composition comprising an exothermic substance, at least one further component selected from the group consisting of water absorptive polymer and a tackifier, at least one further component selected from the group consisting of a carbon component and metal halide, a water content in the composition which is greater than that required as an optimum amount for an exothermic reaction to occur, said exothermic composition is formed as a viscous fluid, and a portion of said water present in said viscous fluid exothermic composition is absorbed by said thin pouch, and said substrate and said covering material are sealed together by a heating technique around at least a part of the area surrounding said viscous fluid exothermic composition.

2. An exothermic device as defined in claim 1, further comprising at least one additional component selected from the group consisting of iron powder, a carbon component and water absorptive agent, said at least one additional component being laminated on an upper surface of said viscous fluid exothermic composition.

3. An exothermic device as defined in claim 1, further comprising iron powder whose particles are coated with a further component selected from the group consisting of a carbon component and a mixture of water, iron powder (A) and a carbon component (B) with the amount of water in the mixture being less than 5% by weight of the sum of (A) and (B) by weight, one of said iron powder or said mixture being laminated on an upper surface of said viscous fluid exothermic composition.

4. An exothermic device as defined in claim 1, wherein at least one of said substrate and said covering material is formed of a film of water absorptive material.

5. An exothermic device as defined in claim 1, further comprising a water absorptive layer formed at least on a portion of said viscous fluid exothermic composition, said portion being in contact with at least one of said substrate and said covering material.

6. An exothermic device as defined in claim 5, wherein said water absorptive layer is formed of a thin sheet of water absorptive material.

7. An exothermic device as defined in claim 1, wherein at least one of said substrate and said covering material is obtained by forming a film of a water absorptive material on at least one of said opposed inner surfaces of a non-gas-permeable film or sheet.

8. An exothermic device as defined in claim 4, wherein said water absorptive material is chosen from the group consisting of:
foamed film or sheet,
papers,
nonwoven or woven fabrics and
porous film or sheet.

9. An exothermic device as defined in claim 5, wherein the water absorptivity of said water absorptive material is improved by the incorporation of a water absorptive agent by a treatment selected from the group consisting of:
soaking,
impregnation,
kneading,
lamination, and
transfer,
causing the water absorptive agent to be carried into the water absorptive material.

10. An exothermic device as defined in claim 1, wherein said substrate and said covering material are formed of an extensible material.

11. An exothermic device as defined in claim 1, wherein, at least one of the following components is gas permeable; one of said opposed surfaces of said pouch, said substrate, said covering material, or a part of at least one of said opposed surfaces of said pouch, said substrate, and said covering material.

12. An exothermic device as defined in claim 1, further comprising an adhesive layer formed on at least a part of an exposed surface of at least one of said substrate and said covering material.

13. An exothermic device as defined in claim 12, wherein said adhesive layer is a wet compress layer containing wet compress agent.

14. An exothermic device as set forth in claim 1, wherein said water content comprises water vapor.

15. An exothermic device as defined in claim 1, further comprising
at least one additional component selected from the group consisting of iron powder, a carbon component and water absorptive agent,
said at least one additional component being sprayed on an upper surface of said viscous fluid exothermic composition.

16. An exothermic device as set forth in claim 1, wherein said heating technique comprises heat-adhesion.

17. An exothermic device as defined in claim 1, wherein at least one of said substrate and said covering material is formed of a thin sheet of water absorptive material.

18. An exothermic device as defined in claim 5, wherein said water absorptive layer is formed of a thin sheet of water absorptive material.

19. An exothermic device as defined in claim 1, wherein at least one of said substrate and said covering material is obtained by forming a film of a water absorptive material on at least one inside surface of a gas-permeable film or sheet.

20. An exothermic device as defined in claim 1, wherein at least one of said substrate and said covering material is obtained by forming a thin sheet of a water absorptive material on at least one inside surface of a non-gas-permeable film or sheet.

21. An exothermic device as defined in claim 12, wherein said adhesive layer is a medication layer containing therein a skin-absorbable drug.

* * * * *